United States Patent [19]
Kitamura et al.

[11] Patent Number: 5,500,354
[45] Date of Patent: Mar. 19, 1996

[54] HEPATIC PARENCHYMAL CELL GROWTH FACTOR GENE ENCODING THE SAME, PROCESS FOR PRODUCING THE FACTOR AND TRANSFORMANTS PRODUCING THE FACTOR

[75] Inventors: Naomi Kitamura, Moriguchi; Keiji Miyazawa, Hirakata; Yasushi Daikuhara; Hirohito Tsubouchi, both of Kagoshima; Daiji Naka, Yokohama; Kazuhiro Takahashi, Machida; Rie Matsui, Tokyo; Yoshiko Yoshiyama; Takehisa Ishii, both of Yokohama, all of Japan

[73] Assignee: Mitsubishi Kasei Corporation, Tokyo, Japan

[21] Appl. No.: 89,417

[22] Filed: Jul. 9, 1993

Related U.S. Application Data

[63] Continuation of Ser. No. 852,758, Mar. 17, 1992, abandoned, which is a continuation of Ser. No. 564,172, Aug. 8, 1990, abandoned.

[30] Foreign Application Priority Data

Aug. 11, 1989 [JP] Japan ..................... 1-209449
Apr. 3, 1990 [JP] Japan ..................... 2-88592
Jul. 27, 1990 [JP] Japan ..................... 2-200898

[51] Int. Cl.$^6$ .......................... C12N 15/16; C12N 15/79; C12N 5/16; C07H 21/04
[52] U.S. Cl. ................. 435/69.4; 435/320.1; 435/240.2; 536/23.51; 935/66; 935/70
[58] Field of Search ................. 435/69.1, 69.3, 435/69.4, 69.6, 70.1, 70.3, 172.3, 240.1, 240.2, 240.21, 320.1; 935/13, 47–51, 70, 71, 66; 536/23.51

[56] References Cited

PUBLICATIONS

Zarnegar, et al., Cancer Research, vol. 49, pp. 3314–3320, 1989.
G. Michalopoulos, et al., Cancer research, 44 pp. 4414–4419, Oct. 1984.
Japanese Patent Application Laid Open (Kokai) No. 45534/85.
R. Zarnegar, et al., Biochemical and Biophysical Research Communiction vol. 163, No. 3, pp. 1370–1376, Sep. 1989.
Nature, vol. 342, No. 23, pp. 440–443, Nov. 1989.
T. Kinoshita, et al., Biochemical and Biophysical Research Communications, vol. 165, No. 3, pp. 1229–1234, Dec. 1989.
R. Zarnegar, et al., Proc. Natl. Acad. Sci. U.S.A., vol. 87, pp. 1252–1256, Feb. 1990.
K. Tashiro, et al., Proc. Natl. Acad. Sci., U.S.A. vol. 87, pp. 3200–3402, Apr. 1990.
F. Thaier, et al., Cancer Research vol. 45, pp. 2545–2549, Jun. 1985.
W. Russell, et al., Journal of Cellular Physiology 119, pp. 183–192 (1984).
H. Nakayama, et al., Biomedical Reseach, 6 (4) 231–237, 1985.
T. Creighton, Proteins, Structures and Molecular Principles, pp. 113–114, 1984.
K. Miyazawa, et al., Biochemical and Biophysical Research Communications, vol. 163, No. 2, pp. 967–973 (15 Sep. 1989).
E. Gohda, et al., J. Clin. Invest., vol. 81, pp. 414–419 (Feb. 1988).
Miyazawa, et al 1989 Biochemical and Biophysical Research Comm. vol. 163 7 pp. 967–973.
Higashio et al. 1990 Biochemical & Biohypical Res. Comm. vol. 170: 397–404.
Derynck, et al 1984 Cell vol. 38: 287–297.
Gohda, et al 1988 J. Clin Invest. 81: 414–419.
Okayoma et al 1983 Mol. Cell. Biol. 3: 280–289.
Moniatis et al Molecular Cloning 1982 pp. 11–15 and 412–431.
Zorvegor et al. 1990 Biochem. & Biophys Res. Comm. 163: 1370–1377.
Nakamura, et al 1990 Nature 324: 440–443.

Primary Examiner—George C. Elliott
Attorney, Agent, or Firm—David G. Conlin; David S. Resnick

[57] ABSTRACT

According to the present invention, there are provided hepatic parenchymal cell growth factor obtained by recombinant DNA technology, a gene coding for the factor, an expression vector capable of expressing the gene, a cell, in particular animal cell, transformed with the expression vector, and a process for producing the hepatic parenchymal cell growth factor.

17 Claims, 10 Drawing Sheets

```
Met Trp Val Thr Lys Leu Leu Pro Ala Leu
                                       10
Leu Leu Gln His Val Leu Leu His Leu Leu
                                       20
Leu Leu Pro Ile Ala Ile Pro Tyr Ala Glu
                                       30
Gly Gln Arg Lys Arg Arg Asn Thr Ile His
                                       40
Glu Phe Lys Lys Ser Ala Lys Thr Thr Leu
                                       50
Ile Lys Ile Asp Pro Ala Leu Lys Ile Lys
                                       60
Thr Lys Lys Val Asn Thr Ala Asp Gln Cys
                                       70
Ala Asn Arg Cys Thr Arg Asn Lys Gly Leu
                                       80
Pro Phe Thr Cys Lys Ala Phe Val Phe Asp
                                       90
Lys Ala Arg Lys Gln Cys Leu Trp Phe Pro
                                      100
Phe Asn Ser Met Ser Ser Gly Val Lys Lys
                                      110
Glu Phe Gly His Glu Phe Asp Leu Tyr Glu
                                      120
Asn Lys Asp Tyr Ile Arg Asn Cys Ile Ile
                                      130
Gly Lys Gly Arg Ser Tyr Lys Gly Thr Val
                                      140
Ser Ile Thr Lys Ser Gly Ile Lys Cys Gln
                                      150
Pro Trp Ser Ser Met Ile Pro His Glu His
                                      160
Ser Phe Leu Pro Ser Ser Tyr Arg Gly Lys
                                      170
Asp Leu Gln Glu Asn Tyr Cys Arg Asn Pro
                                      180
Arg Gly Glu Glu Gly Gly Pro Trp Cys Phe
                                      190
```

FIG. 1a

```
Thr Ser Asn Pro Glu Val Arg Tyr Glu Val
                                        200
Cys Asp Ile Pro Gln Cys Ser Glu Val Glu
                                        210
Cys Met Thr Cys Asn Gly Glu Ser Tyr Arg
                                        220
Gly Leu Met Asp His Thr Glu Ser Gly Lys
                                        230
Ile Cys Gln Arg Trp Asp His Gln Thr Pro
                                        240
His Arg His Lys Phe Leu Pro Glu Arg Tyr
                                        250
Pro Asp Lys Gly Phe Asp Asp Asn Tyr Cys
                                        260
Arg Asn Pro Asp Gly Gln Pro Arg Pro Trp
                                        270
Cys Tyr Thr Leu Asp Pro His Thr Arg Trp
                                        280
Glu Tyr Cys Ala Ile Lys Thr Cys Ala Asp
                                        290
Asn Thr Met Asn Asp Thr Asp Val Pro Leu
                                        300
Glu Thr Thr Glu Cys Ile Gln Gly Gln Gly
                                        310
Glu Gly Tyr Arg Gly Thr Val Asn Thr Ile
                                        320
Trp Asn Gly Ile Pro Cys Gln Arg Trp Asp
                                        330
Ser Gln Tyr Pro His Glu His Asp Met Thr
                                        340
Pro Glu Asn Phe Lys Cys Lys Asp Leu Arg
                                        350
Glu Asn Tyr Cys Arg Asn Pro Asp Gly Ser
                                        360
Glu Ser Pro Trp Cys Phe Thr Thr Asp Pro
                                        370
Asn Ile Arg Val Gly Tyr Cys Ser Gln Ile
                                        380
```

FIG. 1b

```
Pro Asn Cys Asp Met Ser His Gly Gln Asp
                                      390
Cys Tyr Arg Gly Asn Gly Lys Asn Tyr Met
                                      400
Gly Asn Leu Ser Gln Thr Arg Ser Gly Leu
                                      410
Thr Cys Ser Met Trp Asp Lys Asn Met Glu
                                      420
Asp Leu His Arg His Ile Phe Trp Glu Pro
                                      430
Asp Ala Ser Lys Leu Asn Glu Asn Tyr Cys
                                      440
Arg Asn Pro Asp Asp Asp Ala His Gly Pro
                                      450
Trp Cys Tyr Thr Gly Asn Pro Leu Ile Pro
                                      460
Trp Asp Tyr Cys Pro Ile Ser Arg Cys Glu
                                      470
Gly Asp Thr Thr Pro Thr Ile Val Asn Leu
                                      480
Asp His Pro Val Ile Ser Cys Ala Lys Thr
                                      490
Lys Gln Leu Arg Val Val Asn Gly Ile Pro
                                      500
Thr Arg Thr Asn Ile Gly Trp Met Val Ser
                                      510
Leu Arg Tyr Arg Asn Lys His Ile Cys Gly
                                      520
Gly Ser Leu Ile Lys Glu Ser Trp Val Leu
                                      530
Thr Ala Arg Gln Cys Phe Pro Ser Arg Asp
                                      540
Leu Lys Asp Tyr Glu Ala Trp Leu Gly Ile
                                      550
His Asp Val His Gly Arg Gly Asp Glu Lys
                                      560
Cys Lys Gln Val Leu Asn Val Ser Gln Leu
                                      570
```

FIG. 1c

```
                                                          580
Val Tyr Gly Pro Glu Gly Ser Asp Leu Val
                                                          590
Leu Met Lys Leu Ala Arg Pro Ala Val Leu
                                                          600
Asp Asp Phe Val Ser Thr Ile Asp Leu Pro
                                                          610
Asn Tyr Gly Cys Thr Ile Pro Glu Lys Thr
                                                          620
Ser Cys Ser Val Tyr Gly Trp Gly Tyr Thr
                                                          630
Gly Leu Ile Asn Tyr Asp Gly Leu Leu Arg
                                                          640
Val Ala His Leu Tyr Ile Met Gly Asn Glu
                                                          650
Lys Cys Ser Gln His His Arg Gly Lys Val
                                                          660
Thr Leu Asn Glu Ser Glu Ile Cys Ala Gly
                                                          670
Ala Glu Lys Ile Gly Ser Gly Pro Cys Glu
                                                          680
Gly Asp Tyr Gly Gly Pro Leu Val Cys Glu
                                                          690
Gln His Lys Met Arg Met Val Leu Gly Val
                                                          700
Ile Val Pro Gly Arg Gly Cys Ala Ile Pro
                                                          710
Asn Arg Pro Gly Ile Phe Val Arg Val Ala
                                                          720
Tyr Tyr Ala Lys Trp Ile His Lys Ile Ile
Leu Thr Tyr Lys Val Pro Gln Ser
```

FIG. 1d

```
ATG TGG GTG ACC AAA CTC CTG CCA GCC CTG CTG CAG CAT GTC CTC CTG CAT CTC CTC   60
                                        Pst I
CTG CTC CCC ATC GCC CTC CCC TAT GCA GAG GGA CAA AGG AAA AGA AAT ACA ATT CAT  120
GAA TTC AAA AAA TCA GCA AAG ACT ACC CTA ATC AAA ATA GAT CCA GCA CTG AAG ATA AAA  180
Eco RI
ACC AAA AAA GTG AAT ACT GCA GAC CAA TGT GCT AAT AGA TGT ACT AGG AAT AAA GGA CTT  240
                    Pst I
CCA TTC ACT TGC AAG GCT TTT GTT TTT GAT AAA AAA GCA AGA AAA CAA TGC CTC TGG TTC CCC  300
TTC AAT AGC ATG TCA AGT GGA GTG AAA AAA GAA TTT GGC CAT GAA TTT GAC CTC TAT GAA  360
AAC AAA GAC TAC ATT AGA AAC TGC ATC AAA AGT GGC ATC AAA TGT CAG CCC TGG AGT TCC ATG ATA CCA CAC GAA CAC  480
TCT ATC ACT AAG AGT GGC ATC AAA TGT CAG CCC TGG AGT TCC ATG ATA CCA CAC GAA CAC  480
AGC TTT TTG CCT TCG AGC TAT CGG GGT AAA GAC CTA CAG GAA AAC TAC TGT CGA AAT CCT  540
                                                                        Xho I
CGA GGG GAA GAA GGG GGA CCC TGG TGT TTC ACA AGC AAT CCA GAG GTA CGC TAC GAA GTC  600
TGT GAC ATT CCT CAG TGT TCA GAA GTT GAA TGC ATG ACC TGC AAT GGG GAG AGT TAT CGA  660
GGT CTC ATG GAT CAT ACA GAA TCA GGC AAG ATT TGT CAG CGC TGG GAT CAT CAG ACA CCA  720
CAC CGG CAC AAA TTC TTG CCT GAA AGA TAT CCC GAC AAG GGC TTT GAT GAT AAT TAT TGC  780
```

FIG. 2a

```
CGC AAT CCC GAT GGC CAG CCG AGG CCA TGG TGC TAT ACT CTT GAC CCT CAC ACC CGC TGG   840
                                    NcoI
GAG TAC TGT GCA ATT AAA ACA TGC GCT GAC AAT ACT ATG AAT GAC ACT GAT GTT CCT TTG   900
ScaI
GAA ACA ACT GAA TGC ATC CAA GGT CAA GGA GAA GGC TAC AGG GGC ACT GTC AAT ACC ATT   960
TGG AAT GGA ATT CCA TGT CAG CGT TGG GAT TCT CAG TAT CCT CAC GAG CAT GAC ATG ACT  1020
        EcoRI
CCT GAA AAT TTC AAG TGC AAG GAC CTA CGA GAA AAT TAC TGC CGA AAT CCA GAT GGG TCT  1080
GAA TCA CCC TGG TGT TTT ACC ACT GAT CCA AAC ATC CGA GTT GGC TAC TGC TCC CAA ATT  1140
CCA AAC TGT GAT ATG TCA CAT GGA CAA GAT TGT TAT CGT GGG AAT GGC AAA AAT TAT ATG  1200
GGC AAC TTA TCC CAA ACA AGA TCT GGA CTA ACA TGT TCA ATG TGG GAC AAG AAC ATG GAA  1260
GAC TTA CAT CGT CAT ATC TTC TGG GAA CCA GAT GCA AGT AAG CTG AAT GAG AAT TAC TGC  1320
CGA AAT CCA GAT GAT GCT CAT GGA CCC TGG TGC TAC ACG GGA AAT CCA CTC ATT CCT      1380
TGG GAT TAT TGC CCT ATT TCT CGT TGT GCC AAA ACG AAA CAA TTG CGA GTT AAT GGG ATT CCA  1440
GAC CAT CCC GTA ATA AAC ATA GGA TGG ATG GTT AGT TTG AGA TAC AGA AAT AAA CAT ATC TGC GGA  1500
ACA CGA ACA AAC ATA GGA TGG ATG GTT AGT TTG AGA TAC AGA AAT AAA CAT ATC TGC GGA  1560
GGA TCA TTG ATA AAG GAG AGT TGG GTT CTT ACT GCA CGA CAG TGT TTC CCT TCT CGA GAC  1620
                                                                        XhoI
```

FIG. 2b

```
                                                                                        1680
TTG AAA GAT TAT GAA GCT TGG CTT GGA ATT CAT GAT GTC CAC GGA AGA GGA GAT GAG AAA
                                       Eco RI                                           1740
TGC AAA CAG GTT CTC AAT GTT TCC CAG CTG GTA TAT GGC CCT GAA GGA TCA GAT CTG GTT
                                                                                        1800
TTA ATG AAG CTT GCC AGG CCT GCT GTC CTG GAT GAT TTT GTT AGT ACG ATT GAT TTA CCT
                                                                                        1860
AAT TAT GGA TGC ACA ATT CCT GAA AAG ACC AGT TGC AGT GTT TAT GGC TGG GGC TAC ACT
                                                                                        1920
GGA TTG ATC AAC TAT GAT GGC CTA TTA CGA GTG GCA CAT CTC TAT ATA ATG GGA AAT GAG
                                                                                        1980
AAA TGC AGC CAG CAT CAT CGA GGG AAG GTG ACT CTG AAT GAG TCT GAA ATA TGT GCT GGG
                                                                                        2040
GCT GAA AAG ATT GGA TCA GGA CCA TGT GAG GGG GAT TAT GTT CCT GGT GGC CCA CTT TGT GAG
                                                                                        2100
CAA CAT AAA ATG AGA ATG GTT CTT GGT GTC ATT GTT CCT GGT CGT GGA TGT GCC ATT CCA
                                                                                        2160
AAT CGT CCT GGT ATT TTT GTC CGA GTA GCA TAT TAT GCA AAA TGG ATA CAC AAA ATT ATT
TTA ACA TAT AAG GTA CCA CAG TCA TAG
                 Kpn I
```

FIG. 2c

HEPATIC PARENCHYMAL CELL GROWTH FACTOR GENE ENCODING THE SAME, PROCESS FOR PRODUCING THE FACTOR AND TRANSFORMANTS PRODUCING THE FACTOR

This is a continuation of application Ser. No. 07/852,758 filed on Mar. 17, 1992, and now abandoned, which is a continuation of application Ser. No. 07/564,172, now abandoned.

BACKGROUND OF THE INVENTION

1. Field of the Invention

This invention relates to a hepatic parenchymal cell growth factor obtained by the recombinant DNA technology; to a gene encoding it; to a transformant carrying an expression vector which comprises at least a promoter sequence required for the expression of a protein, a sequence encoding a signal peptide, a DNA sequence encoding human hepatic parenchymal cell growth factor, and a terminator sequence; and to a process for the production of human hepatic parenchymal cell growth factor by culturing the transformant.

2. Description of the Prior Art

The liver is the most highly differentiated and largest adenogenous organ in a living body. It exhibits various important functions such as treatment (metabolism), storage, detoxication, decomposition, excretion and the like of various nutritive substances (carbohydrates, proteins, lipids, vitamins, hormones and the like), and especially it plays an important role in the intermediate metabolism of a living body.

These functions are sustained by hepatic parenchymal cells which are controlled by various hormones in a living body and may show remarkably active proliferation in certain cases. In a rat, for example, it has been known that even after surgical resection of about two-thirds of the liver the remaining hepatic tissue promptly grows and may be restored to its original size in about 10 days. On the other hand, patients suffering from hepatic carcinoma have been treated by partial hepatectomy followed by regeneration.

A large number of researches and investigations have been pursued to elucidate the mechanism of hepatic regeneration by the proliferation of hepatic parenchymal cells, with reports suggesting the presence of hepatic parenchymal cell growth factor. Especially, some of the present inventors found that plasma from patients with fulminant hepatitis had a markedly high activity to proliferate hepatic parenchymal cells (*Biomed. Res.*, 6, 231 (1985) and *Exp. Cell Res.*, 166, 139 (1986)) and succeeded for the first time in the world in purifying the proliferation-activating factor as a single protein (Japanese Patent Application Kokai No. 22526/1988 and *J. Clin. Invest.*, 81, 414 (1988)).

This human hepatic parenchymal cell growth factor (human hepatocyte growth factor; to be referred to as "hHGF" hereinafter) had a molecular weight of approximately 76,000 to 92,000 as estimated by SDS-PAGE under non-reducing conditions, but SDS-PAGE under reducing conditions revealed two bands at molecular weights of 56,000 to 65,000 and 32,000 to 35,000. Nakamura et al. reported rat platelet derived factor having similar activity (*Biochem. Biophys. Res. Commun.*, 122, 1450 (1984)), and estimated its molecular weight to be approximately 27,000 by SDS-PAGE (*Proc. Natl. Acad. Sci. USA*, 83, 6489 (1986)). Thereafter, they purified the factor as a homogeneous protein and reported that the purified factor was a protein having a molecular weight of 82,000, which consisted of two polypeptides having molecular weights of 69,000 and 34,000 (FEBS Letters, 224, 311 (1987)).

Except for the above mentioned hHGF and rat HGF, there has been no report on any hepatocyte growth factor which has been purified as a homogeneous protein. Even with regard to the hHGF and rat HGF, we know of no report concerning their primary structures and corresponding cDNA base sequences.

A large amount of hHGF will be required when an examination is to be performed in order to elucidate the function of hHGF in a living body in detail and/or its effects on the hepatic regeneration in a patient with hepatopathy. However, isolation and purification of a large amount of hHGF from plasma of patients with fulminant hepatitis are not so easy in view of labor, time and economy, and stable isolation of only hHGF from sera in which various infectious agents exist is extremely difficult to achieve. Because of these reasons, stable and large scale isolation and purification of hHGF from plasma of patients with fulminant hepatitis have not been attempted.

SUMMARY OF THE INVENTION

The present inventors have conducted intensive studies for the purpose of obtaining a large amount of hHGF by the recombinant DNA technology and succeeded for the first time in cloning a gene coding for hHGF, which is useful for such a purpose. Further, the present inventors have constructed a new expression vector containing the gene, enabling the expression of hHGF. Thus, the present invention has been attained.

Accordingly, it is an object of the present invention to provide a hepatic parenchymal cell growth factor obtained by the genetic engineering.

Another object is to provide a gene coding for such a hepatic parenchymal cell growth factor.

Still another object is to provide an expression vector containing the gene.

A further object of the present invention is to provide a transformant, for example, an animal cell, carrying the expression vector, which is capable of producing the hepatic parenchymal cell growth factor.

A still further object is to provide a process for producing the hepatic parenchymal cell growth factor by the recombinant DNA technology.

The other objects of the present invention will be apparent from the following description.

BRIEF DESCRIPTION OF THE DRAWINGS

The invention will be better understood by the following description with reference to the attached drawings in which:

FIG. 1a to d show the amino acid sequence of the hHGF of the present invention;

FIG. 2a to c show the base sequence of the cDNA obtained in Example 1, which contains a gene coding for the hHGF of the present invention. Recognition sites of principal restriction enzymes are also shown in this figure. Underlines in the figure indicate the regions which correspond to the amino acid sequences already determined, and, of these, double underlines indicate the sequences that correspond to the probe used in the first cloning according to the present invention;

DESCRIPTION OF THE INVENTION

Figure 3:
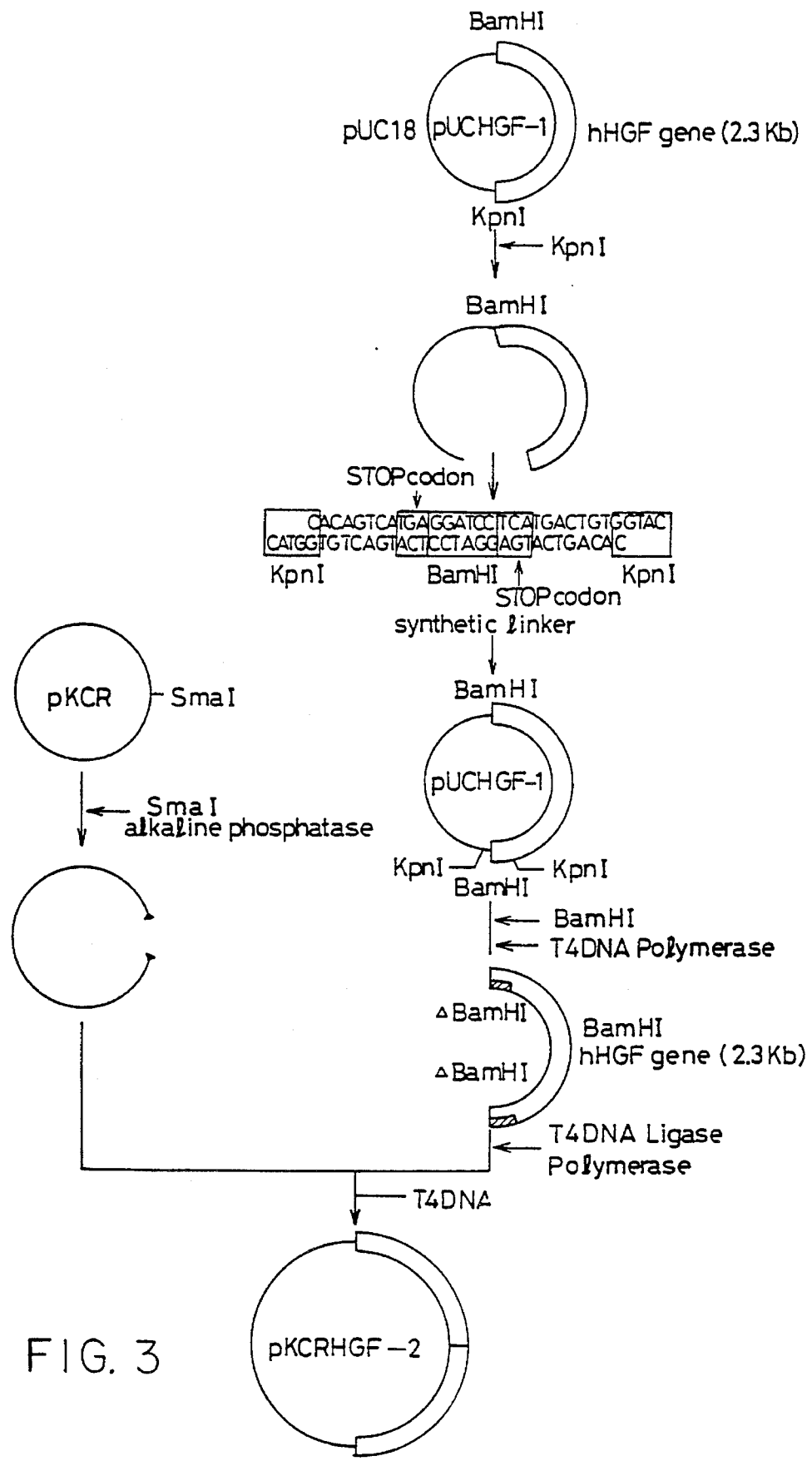
FIG. 3 shows a scheme for the construction of a vector capable of expressing human parenchymal cell growth factor.

According to the present invention, there are provided human hepatocyte growth factor (hHGF) represented by the amino acid sequence as shown in FIG. 1, which contains a signal sequence; hHGF represented by the amino acid sequence ranging from the 30th glutamic acid residue (Glu) to the last serine residue (Ser) in FIG. 1; and hHGF represented by the amino acid sequence ranging from the 32nd glutamine residue (Gln) to the last serine residue (Ser) in FIG. 1. Also provided are a gene coding for the hHGF represented by any of said amino acid sequences; the gene represented by the base sequence as shown in FIG. 2, which codes for hHGF containing a signal sequence; the gene represented by the base sequence ranging from the 88th base, guanine (G), to the last base (G) in FIG. 2; and the gene represented by the base sequence ranging from the 94th base, cytosine (C), to the last base (G) in FIG. 2. The present invention also provides a process for producing hHGF represented by the amino acid sequence of FIG. 1 which comprises transforming a host cell with an expression vector containing a gene coding for the hHGF, and culturing the resulting transformant. Further, a transformant capable of producing the hHGF is provided according to the present invention.

The gene (cDNA) coding for the hHGF of the present invention may have the base sequence as shown in FIG. 2, in which, however, only the base sequence of a single-stranded DNA is described while complementary base sequences are omitted as a matter of convenience.

The gene may be used to express hHGF having the amino acid sequence as shown in FIG. 1 by the recombinant DNA technology. In that case, a protein translated from the corresponding mRNA coding for the hHGF contains a signal sequence. This signal sequence will be cleaved off when the protein is secreted from host cells, thus resulting in the production of hHGF having the amino acid sequence which ranges from the 30th glutamic acid residue (Glu) or the 32nd glutamine residue (Gln) to the last amino acid residue of the sequence represented by FIG. 1. Instead of this signal sequence, certain signal sequences of other proteins may also be used herein. On the other hand, when mature hHGF having no signal sequence is to be expressed in host cells, an hHGF-encoding gene having the base sequence which ranges from the 88th G or the 94th C to the last base of the sequence represented by FIG. 2, may be used after ligating the gene with an ATG codon of a vector DNA.

In accordance with the present invention, it is intended to include all modifications such as elimination, change, and addition of one or more amino acids or nucleic acids, provided that the growth-enhancing activity of the hepatic parenchymal cells is not altered.

A DNA fragment of a gene coding for hHGF of the present invention may be obtained by the following procedures:

According to the method described in J. Clin. Invest., 81, 414 (1988), hHGF may be purified from plasma of patients with fulminant hepatitis. The purified hHGF will be dissociated into two polypeptides by the breakage of disulfide bonds under reducing conditions. The larger polypeptide having a molecular weight of 56,000 to 65,000 is called "H chain", and the smaller one having a molecular weight of 32,000 to 35,000 "L chain".

The purified hHGF is reduced and the thiol groups of cystein residues formed are carboxymethylated followed by subjecting to reverse-phase high-pressure liquid chromatography to isolate the H and L chains. Alternatively, hHGF may be electrophoresed under a reducing condition on a gel, from which each of the H and L chains is extracted. The N-terminal amino acid sequences of the both chains may then be determined by analyzing the chains by Applied Biosystems gas phase protein sequencer.

On the other hand, hHGF itself, of after separating it into H and L chains, may be hydrolyzed by an appropriate proteolytic enzyme, such as *Achromobacter* Protease I (lysyl endopeptidase). The resulting peptide fragments may be isolated by reverse-phase high-pressure liquid chromatography. Each peptide may be analyzed as described above to determine an internal amino acid sequence of the polypeptide.

From these amino acid sequences, DNA base sequences may be deduced to select a sequence suitable for the preparation of an oligonucleotide, for example, the one as shown in Examples described hereinbelow. Such an suitable oligonucleotide is synthesized and used as a probe.

A cDNA library to be screened for a gene coding for hHGF may be any one derived from human liver, spleen or placenta and is commercially available from Clontech Laboratories, Inc. A placental cDNA library is particularly preferred. Further, cDNA library may also be prepared in a usual manner from a cell line or tissue material in which hHGF is expressed.

*E. coli* is infected with lambda phage which contains such a cDNA and cultured, in accordance with the method of Maniatis (Molecular Cloning, A Laboratory Manual, pages 56 to 73, Cold Spring Harbor Laboratories, 1982). Plaques thus formed are then subjected to a selection process using as a probe an oligonucleotide prepared above based on the base sequence deduced from a portion of the amino acid sequence of hHGF, according to the plaque hybridization method (Molecular Cloning, A Laboratory Manual, pages 320 to 328, Cold Spring Harbor Laboratory, 1982). Thus, several different lambda phage clones may be easily obtained, each clone having both the base sequence used as the probe and a base sequence corresponding to the other region of the amino acid sequence of the desired hHGF.

The positive plaques in the screening process are selected and the phages are grown according to the method of Maniatis (Molecular Cloning, A Laboratory Manual, pages 76 to 79, Cold Spring Harbor Laboratory, 1982). DNA is purified by the glycerol gradient method and digested with an appropriate enzyme, such as EcoRI. The resulting cDNA is then subcloned into a plasmid vector, such as pUC18 and pUC19, or a single stranded phage, such as M13mp18 and M13mp19. The base sequence of a desired cDNA segment may be determined according to the dideoxy chain termination method of Sanger et al. (Proc. Natl. Acad. Sci. USA, 74, 5463 (1977)). In this manner, the obtained cDNA subclones are analyzed to determine the base sequences, which may code for different portions of hHGF and be combined (FIG. 2). Thus, the whole base sequence of a gene coding for the entire amino acid sequence of hHGF as shown in FIG. 1 may be determined.

Industrial production of hHGF will require the selection of a host-vector system capable of providing stable expression. Also, expressed hHGF must possess the biological activity to proliferate hepatic parenchymal cells. In particular, it should be taken into consideration that naturally occurring hHGF is a glycoprotein, that hHGF contains a number of cyteine residues, and that the positions of disulfide bonds formed between thiol groups in the cysteine residues and the higher order structure play an important role in maintaining the activity of hHGF.

Taking the above into consideration, it is desirable to use animal cells, for example, CHO, COS, and mouse L, C127 and FM3A cells, as host cells ,for expressing the hHGF gene according to the present invention, although microorganisms, such as yeast, eg., *Saccharomyces cerevisiae,* and *Escherichia coli,* eg., *E. coli* YA-21, may be used. Further, when such an animal cell is used as a host cell, it will be advantageous that a gene coding for immature hHGF containing a signal sequence, i.e., such a gene that also contains 1 to 87, or 1 to 93 nucleotides of the DNA sequence as shown in FIG. 2, is used and incorporated into the cell, since the mature hHGF protein is expected to be secreted in culture media.

An expression vector which may be used in the present invention contains a DNA fragment coding for at least a portion of the amino acid sequence of the hHGF protein downstream from the promoter of the vector. It may be contemplated herein to use various promoters, including SV40 promoter, the promoters of apolipoprotein E and A1 genes, of heat shock protein gene, and of metallothionein gene, HSV TK promoter, adenovirus promoter, and retrovirus LTR. In the present invention, however, SV40 promoter or the promoter of metallothionein gene is preferred.

A DNA fragment coding for immature hHGF containing a signal sequence is inserted into a vector downstream from its promoter in the direction of transcription. It is possible to insert a combination of two or three such hHGF DNA fragments. Also, it may be possible to prepare such a unit that comprises an hHGF DNA fragment, 5' upstream of which a promoter is linked to, and to insert two or three such units into a vector in tandem along the direction of transcription.

A polyadenylation signal should be present downstream from the hHGF gene in the expression vector. Such a polyadenylation signal may be derived from SV40 DNA, beta-globin gene, or metallothionein gene. When two or three DNA fragments comprising a promoter linked to the hHGF gene as described above are inserted in tandem into a vector, it is possible to link a polyadenylation signal to 3' of each hHGF gene.

It is desirable to use a selective marker when an animal cell such as CHO cell is transformed with the expression vector. Such a selective marker gene may be inserted into the expression vector downstream from the polyadenylation signal along or against the direction of transcription, otherwise another plasmid containing a selective marker gene must be co-transformed to obtain a transformant. Such selective markers may include DHFR gene providing methotrexate resistance (J. Mol. Biol., 159, 601 (1982)); Neo gene providing G-418 antibiotic resistance (J. Mol. Appl. Genet., 1, 327 (1982)); *E. coli* derived Ecogpt gene providing mycophenolic acid resistance (Proc. Natl. Acad. Sci. USA, 78, 2072 (1981)); and hph gene providing hygromycin antibiotic resistance (Mol. Cell. Biol., 5, 410 (1985)). The selective marker gene has a promoter, for example, SV40 promoter, 5' upstream thereof and a polyadenylation signal 3' downstream therefrom.

As already described, when such a selective marker gene is not inserted into the expression vector, another vector or plasmid which contains a marker enabling the selection of a transformant may be co-transformed into a host cell together with the expression vector containing hHGF gene. Such vectors may include pSV2neo (J. Mol. Appl. Genet., 1, 327 (1982)); pMBG (Nature, 294, 228 (1981)); pSV2gpt (Proc. Natl. Acad. Sci. USA, 78, 2072 (1981)); and pAd-D26-1 (J. Mol. Biol., 159, 601 (1982)). In this case, a transformant may be easily selected on the basis of the phenotype of the selective marker used.

In the above mentioned selection methods, those cells containing the desired hHGF protein gene may be repeatedly subjected to co-transformation using a different selective marker. This may preferably increase about 20 fold the amount of protein expressed.

Introduction of the expression vector into animal cells may be conducted by the calcium phosphate method (Virology, 52, 456 (1973)) or the electroporation method (J. Membr. Biol., 10, 279 (1972)). The calcium phosphate method is commonly used.

Animal cells thus transformed may be cultured in conventional manners by suspension or adhesion culture. MEM or RPMI1640 may be used as a culture medium and the culture may be carried out in the absence of presence of 5–10% serum and in the presence of an appropriate amount of insulin, dexamethasone or transferrin.

The animal cells producing the hHGF protein will secrete the produced hHGF protein into culture media. The hHGF protein can be purified and isolated from the supranatant of the culture. Specifically, the supernatant may be subjected to a combination of various chromatographic operations on S-Sepharose, heparin-Sepharose, hydroxyapatite, and/or sulfated cerulophain to purify and isolate hHGF protein.

According to the present invention, hHGF (prehHGF) having the amino acid sequence starting from Met as shown in FIG. 1 is first expressed in host cells. The hHGF (prehHGF) is then hydrolyzed between the 31st Gly and the 32nd Gln in the host cells; thus, the signal peptide of 31 amino acids is cleaved off. The N-terminal Gln is then deaminated to be converted into pyroglutamic acid. Thus, hHGF having pyroglutamic acid residue at its N-terminus is secreted.

In the hHGF of the present invention, the peptide chain from the N-terminal pyroglutamic acid to the 494th Arg constitutes the heavy (H) chain while the remaining peptide from the 495th Val to the last Ser the light (L) chain.

In accordance with the present invention, the hHGF protein having biological activities can be produced abundantly, stably and easily by introducing, into a host cell, an expression vector into which the hHGF gene of the present invention has been inserted. Such production of hHGF has not been attained prior to the present invention. Thus obtained recombinant hHGF, hHGF-like substances or hHGF-containing fused proteins may be used in the treatment of hepatic diseases as hepatic regeneration-enhancing, hepatic function-improving, hepatitis-curing, hepatic cirrhosis-suppressing agents.

EXAMPLES

The following examples will be given by way of illustration only. The present invention is not limited to these examples. It should be understood that those skilled in the art may make many modifications without departing from the spirit and scope of the present invention as defined in the attached claims.

Example 1

[1] Determination of partial amino acid sequence of hHGF and preparation of a probe Purification of hHGF from plasma of patients with fulminant hepatitis was performed in accordance with the method described in *J. Clin. Invest.*, 81, 414 (1988). Thus purified hHGF preparation was subjected to SDS-PAGE. A relatively broad single band was observed at molecular weights from 76,000 to 92,000 under non-reducing condition. SDS-PAGE under reducing condition, on the contrary, has revealed two bands; a relatively broad band at molecular weights of 56,000 to 65,000 and the other band at molecular weights of 32,000 to 35,000. A 50 μg portion of the purified hHGF preparation was dissolved in 100 μl of 50 mM Tris-HCl buffer (pH 9) containing 5M urea, and the resulting solution was mixed with an amount of *Achromobacter Protease* I equivalent to 1/200 of hHGF in molar ratio, followed by incubation at 37° C. for 6 hours. The resulting peptide mixture was subjected to reduction and carboxymethylation in convention manners. Each peptide was then separated and isolated by means of reverse-phase high-pressure liquid chromatography using Bakerbond WP Octyl Column (J. T. Baker). Analyses of four peptides using a gas phase protein sequencer (Applied Biosystems; Model 470A) revealed their amino acid sequences as shown in the following Table 1.

TABLE 1

Amino acid sequences of peptides

| Peptide No. | Sequence |
|---|---|
| 1. | Phe Leu Pro Glu Arg Tyr Pro Asp Lys |
| 2. | Glu Phe Gly His Glu Phe Asp Leu Tyr Glu Asn Lys |
| 3. | Asp Tyr Glu Ala Trp Leu Gly Ile His Asp Val His Gly Arg Gly Asp XXX*Lys |
| 4. | Asn Met Glu Asp Leu His Arg His Ile Phe Trp Glu Pro Asp Ala Ser Lys |
| 5. | Arg Arg Asn Thr Ile His Glu Phe Lys |
| 6. | Ile Asp Pro Ala Leu Lys |

*XXX indicates an amino acid not determined

Next, synthetic oligonucleotides were prepared based on the partial amino acid sequences, Asn-Met-Glu-Asp-Leu-His and His-Ile-Phe-Trp-Glu-Pro, of the peptide No. 4 shown in Table 1. That is, 64 oligonucleotides TH23 consisting of 17 bases (5'-T-G-T/C/A/G-A-A/G-A/G-T-C-T/C-T-C-C-A-T-A/G-T-T-3') and 24 oligonucleotides TH24 consisting of 17 bases (5' -G-G-T/C-T-C-C-C-A-A/G-A-A-A/G/T-A-T-A/G-T-G-3') were prepared. The 5' end of each synthetic oligonucleotide was labeled with $^{32}P$ in a conventional manner using polynucleotide kinase in a reaction solution (50 mM Tris-HCl (pH 7.6), 10 mM magnesium chloride, 10 mM mercaptoethyl alcohol, 100 μM [$\gamma^{32}P$] ATP and substrate DNA). Unnecessary mononucleotides in these labeled samples were removed by conventional DEAE cellulose column chromatography.

[2] Screening of cDNA coding for a portion of hHGF (1) Plaque hybridization

γ phage cDNA library (Clontech Laboratories, Inc.) originated from 34-week-old human placenta was screened according to the manufacturer's specifications. *E. coli* Y-1090 strain was infected with phages of 1,000,000 clones and cultured at 42° C. overnight on an NZY soft agar medium using five Petri dishes (24.5 cm×24.5 cm), each dish containing 200,000 clones (NZY medium; 1% NZ-Amine, 0.5% yeast extracts and 0.5% sodium chloride, adjusted to pH 7.5 and supplemented with 0.25% magnesium chloride, and NZY soft agar medium; NZY medium supplemented with agar powder to its final concentration of 0.7% and autoclaved).

Next, the resulting γ phage clones grown on the medium were transferred on a commercial nylon membrane (Gene Screening Plus, Du Pont Company) and subjected to plaque hybridization as follows.

Phage particles grown on one dish were transferred on two nylon membranes and each membrane was put on a filter paper impregnated with 0.1M sodium hydroxide and 1.5M sodium chloride. After standing still for 2 minutes on the filter paper, moisture of the nylon membrane was removed by using another dry filter paper. The thus dried membrane was then placed on another filter paper impregnated with 2×SSCP—0.2 M Tris-HCl (pH 7.4), stood still on the filter paper and then air-dried on another dry filter paper. These procedures were repeated again. The term "2×SSCP" means double concentration of SSCP solution and similar way of expressions are used hereinafter (10×SSCP; 1.2 M sodium chloride, 150 mM sodium citrate, 130 mM potassium dihydrogenphosphate and 1 mM EDTA and pH 7.2).

Thus treated nylon membrane was washed at 60° C. for 15 minutes with 3×SSC—0.1% SDS (20×SSC; 3 M sodium chloride and 0.3M sodium citrate). The washing process was repeated again. Each of the thus washed nylon membrane was then incubated at 65° C. for 3 hours in 5 ml of a pre-hybridization solution [3×SSC, 0.1% SDS, 10×Denhalt (50×Denhalt solution; 1% BSA (bovine serum albumin), 1% polyvinyl pyrrolidone and 1% Ficol 400), and 20 μg/ml of salmon sperm DNA]. The foregoing nylon membranes were incubated for 36 hours in a hybridization solution containing the $^{32}P$-labeled synthetic oligonucleotide probe prepared in [1] above [3× SSC, 10×Denhalt, 50 μg/ml of salmon sperm DNA, 1M sodium chloride, 1% SDS, 250 μg/ml of salmon sperm DNA and 100,000 c.p.m./ml of $^{32}P$-labeled probe DNA per each synthesized probe]. The incubation temperature was calculated by regarding A or T as 2° C. and G or C as 4° C. and totaling these values of each probe (42° C. in the case of the TH23 probe and 46° C. in the case of the TH24 probe). Thereafter, the thus incubated nylon membranes were removed from the hybridization solution, washed twice in 4×SSC (30 minutes for each) at room temperature, washed twice in 4×SSC (30 minutes for each) at the foregoing hybridization temperature, again washed twice in 2×SSC (15 minutes for each) at room temperature, and then subjected to autoradiography.

A total of 6 autoradiographic signals which coincided with one another between a pair of the nylon membranes were found. In order to isolate clones corresponding to these signals, each of the plaques on the foregoing soft agar medium, which coincided with these positive signals, was removed using a glass tube. Phage particles in the thus removed plaque were extracted by incubating the plaque overnight in 1 ml of TMG buffer [50 mM Tris-HCl (pH 7.5), 100 mM sodium chloride, 10 mM magnesium chloride and 0.01% gelatin] in the presence of 50 μl of chloroform. *E. coli* Y-1090 cells were infected with the thus extracted phage particles, and an appropriate amount of the infected cells was cultured on the soft agar medium in a Petri dish (9 cm in diameter). The plaque hybridization was carried out as previously described. By repeating a series of these procedures, each clone corresponding to the positive autoradiographic signal was isolated.

As a result, a total of 6 independent clones were obtained. Of these, two clones, named γ hHGF21 and γ hHGF502, were subjected to the analysis of their cDNA base sequences.

(2) Subcloning of cDNA fragments and determination of base sequences

DNA fragments were extracted from the γ phage clones and subcloned into plasmid vectors pUC18 and pUC19 and single strand phage vectors M13mp18 and M13mp19 as follows.

Infection of 40 µl suspension of $2 \times 10^8$ cells of *E. coli* Y-1090 strain with $2 \times 10^7$ p.f.u. (plaque formation unit) of γ phage clone suspended in 200 µl of TMG solution was performed by incubating them at 37° C. for 15 minutes in 200 ml of NZY medium in a 500 ml conical flask. Immediately after the incubation, 1 ml of 1M calcium chloride solution was added and the culture was incubated overnight (about 14 hours).

To the culture was added 2 ml of chloroform. After standing still for about 10 minutes, 15.8 g of sodium chloride was added and dissolved. Centrifugation was carried out at 6,000 rpm for 20 minutes at 4° C. using a refrigerated centrifuge (model SCR 20BB; rotor, RPR 9-2; Hitachi Ltd.). A 20 g portion of polyethylene glycol 6,000 was added to the resulting supernatant fluid and dissolved thoroughly. After standing still for 1 hour in an ice bath, the resulting mixture was centrifuged at 6,000 rpm for 20 minutes using Hitachi refrigerated centrifuge, model SCR 20BB, and the rotor, RPR 9-2. Resulting pellet was suspended in 6 ml of buffer A [0.5% NP40, 36 mM calcium chloride, 30 mM Tris-HCl (pH 7.5), 50 mM magnesium chloride, 125 mM potassium chloride, 0.5 mM EDTA, 0.25% deoxycholic acid and 0.6 mM mercaptoethanol]. The suspension was then mixed with 100 µl of 10 mg/ml Deoxyribonuclease I and 10 µl of 10 mg/ml Ribonuclease A and incubated at 30° C. for 30 minutes in order to hydrolyze *E. coli*-originated nucleic acids. Thereafter, the reaction mixture was mixed with an equal volume of chloroform and stirred thoroughly followed by centrifugation 3,000 rpm for 10 minutes (model LC-06; rotor, TS-7; Tomy Seiko Co., Ltd.) to obtain supernatant fluid.

On the other hand, a double-layer glycerol solution was prepared in a centrifugal tube for ultracentrifugation (rotor, RPS40T; Hitachi Ltd.) by firstly charging the tube with 1 ml of a 40% glycerol solution [0.5% NP40, 30 mM Tris-HCl (pH 7.5), 125 mM potassium chloride, 0.5 mM EDTA, 0.6 mM mercaptoethanol and 40% glycerol] and then by placing thereon 3 ml of a 10% glycerol solution [0.5% NP40, 30 mM Tris-HCl (pH 7.5), 125 mM potassium chloride, 0.5 mM EDTA, 0.6 mM mercaptoethanol and 10% glycerol]. On the double-layer solution was overlaid the nuclease-treated phage suspension. After centrifugation at 35,000 rpm for 1 hour (model 70P72; rotor, RPS40T; Hitachi Ltd.), phage particles recovered as the pellet in the tube were suspended in 0.4 ml of 40 mM Tris-HCl (pH 7.5), 10 mM EDTA and 2% SDS and the suspension was incubated at 55° C. for 1 hour in the presence of 4 µl of 10 mg/ml Proteinase K. Thereafter, the resulting solution was transferred into an Eppendorf tube, and the phage DNA was extracted with an equal volume of phenol/chloroform and recovered by ethanol precipitation. In this way, 200 µg of the phage DNA was obtained.

The phage DNA was digested with restriction enzyme EcoRI in a conventional manner and the digests were analyzed by agarose gel electrophoresis. Three EcoRI fragments of 0.2 kb, 0.85 kb and 0.72 kb in size were obtained from the clone, γ hHGF21. On the other hand, cDNA fragments were obtained by recovering the insert cDNA fragments from the agarose gel by conventional methods.

A 100 ng portion of each of these cDNA fragments and a 200 ng portion of each of plasmid vectors pUC18 and pUC19 and single strand phage vectors M13mp18 and M13mp19, which had been digested in advance with restriction enzyme EcoRI in conventional manners, were incubated in the presence of T4 DNA ligase in 10 µl of a reaction solution [66 mM Tris-HCl (pH 7.6), 6.6 mM magnesium chloride, 10 mM dithiothreitol, 66 µM ATP and substrate DNA]. Each of the ligated DNA samples was used to transform *E. coli* host selected in accordance with the used vector by conventional methods. As a result, subclones containing a partial base sequence of HGF gene in the EcoRI insert site were obtained.

Determination of base sequences of the cDNA subclones was performed in accordance with Sanger et al. dideoxy chain termination method. Primers which corresponded to commercially available M13 phage vectors were selected.

Deduction of amino acid sequence from the base sequence of the clone γ hHGF21 which had the longest cDNA revealed that the amino acid sequence of this clone contained some of the already determined partial amino acid sequence, which were different from the amino acid sequence used for the construction of probe, thus showing that this clone comprised a cDNA coding for at least a part of the hHGF.

Further, when cDNA base sequence of another clone γ hHGF502 which contained a different cDNA fragment that did not exist in the γ hHGF21, was analyzed in accordance with Sanger et al. method, it was found that the phage clone γ hHGF502 possessed a common 0.8 kb base sequence of the phage clone γ hHGF21, i.e., the sequence which ranged from a base around the restriction enzyme NcoI site to a base around the third EcoRI cleavage site from 5' upstream as shown in FIG. 2, as well as a 0.7 kb base sequence at 3' side of the common sequence, which was not found in γ hHGF21. It was also found that the base sequence of γ hHGF502, which was not included in the base sequence of γ hHGF21, contained a partial base sequence which corresponded to one of the already determined partial amino acid sequence of hHGF. It was further found that the whole amino acid sequence of hHGF was covered up by combining the base sequences of these two clones in such a way that the common parts of their base sequences were overlapped.

EXAMPLE 2

(I) Preparation of hHGF Expression Plasmid

FIG. 3 shows the scheme used for the preparation of an hHGF expressing plasmid.

According to the conventional method described in "Molecular Cloning", Cold Spring Harbor Laboratory, p. 93 (1982), plasmid pUCHGF-1 DNA was prepared, which comprised a BamHI-KpnI fragment containing hHGF cDNA (Blochem. Biophys. Res. Commun., 163(2), 967–973 (1989)). The BamHI-KpnI fragment of about 2.3 kb in size extended from the BamHI site at 27 base upstream of the initiation codon ATG to the KpnI site at 8 base upstream of the stop codon TAG.

The plasmid DNA (10 ug) was digested with KpnI restriction enzyme in a conventional manner. The resulting DNA fragment was extracted with phenol/chloroform, purified by ethanol precipitation, and dissolved in 10 ul water.

Into the KpnI cleavage site of the DNA fragment, a synthetic linker of 32 bases was introduced according to Maniatis et al. method described in "Molecular Cloning", Cold Spring Harbor Laboratory, 396–397 (1982)). The linker had KpnI site at both ends thereof and contained therein a stop codon TGA and a BamHI cleavage site, as shown in FIG. 3.

The thus modified plasmid was used to transform *E. coli* in a conventional manner. From the resulting transformants, plasmid DNA was prepared in accordance with the conventional method described in "Molecular Cloning", Cold Spring Harbor Laboratory, p. 93 (1982).

The plasmid DNA (10 ug) was digested with BamHI restriction enzyme in a conventional manner. The resulting reaction mixture was subjected to 1.0% agarose gel electrophoresis to isolate the hHGF DNA fragments containing ATG initiation and TGA stop codons from concomitant undesirable DNA fragments.

From the agarose gel, BamHI-BamHI DNA fragment of about 2.3 kb coding for hHGF was prepared according to Maniatis et al. method described in "Molecular Cloning", Cold Spring Harbor Laboratory, p. 164 (1982). The DNA fragment was treated with T4 DNA polymerase in a conventional manner to form blunt ends at both termini thereof. The blunt-ended DNA fragment was extrated with phenol/chloroform, purified by ethanol precipitation, and dissolved in 10 ul water.

On the other hand, 0.05 ug of expression vector pKCR as described in Proc. Natl. Acad. Sci., 78, 1527 (1981) was digested with SmaI restriction enzyme to form blunt ends in a conventional manner, extracted with phenol/chloroform, and purified by ethanol precipitation. The vector DNA was dissolved in 400 ul of 50 mM Tris-HCl (pH 8), 1 mM magnesium chloride, and dephosphorylated with 1 unit of bacterial alkaline phosphatase (TOYOBO, BAP-101) at 65° C. for 30 minutes. The DNA fragment was then extracted with phenol/chloroform, purified by ethanol precipitation, and dissolved in 10 ul water.

The vector pKCR DNA fragment (0.01 ug) prepared above was ligated to the blunt-ended BamHI hHGF cDNA fragment (0.1 ug) in the presence of T4 DNA ligase (TOYOBO, LGA-101) in 20 ul of 66 mM Tris-HCl (pH 7.6), 6.6 mM magnesium chloride, 10 mM dithiothreitol, 66 uM ATP at 14° C. for 12 hours.

The resulting reaction mixture (10 ul) was used to transform *E. coli* HB 101 (Takara Shuzo) according to the specification. The transformants were cultured on a medium containing 50 ug/ml ampicillin. Several tens of ampicillin resistant strains were obtained.

Plasmids from these strains were analyzed in accordance with Maniatis et al. method described in "Molecular Cloning", Cold Spring Harbor Laboratory, 86–96 (1982). Thus, plasmid pKCRHGF-2 was obtained, in which two hHGF genes had been incorporated in tandem into the SmaI cleavage site present between the promoter and polyadenylation signal in the expression vector pKCR.

Figure 4:
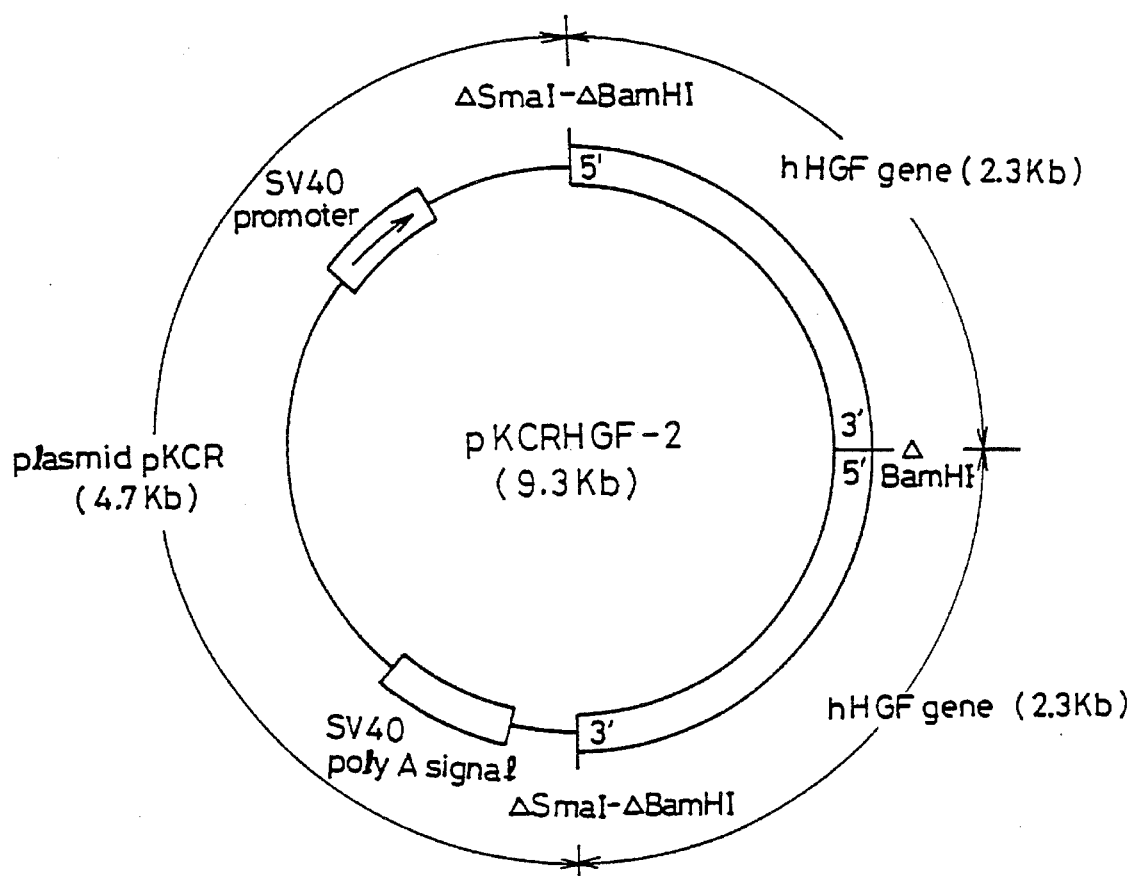
FIG. 4 shows the structure of an expression vector containing the DNA coding for the human parenchymal cell growth factor according to the present invention.

The structure of the plasmid pKCRHGF-2 is shown in FIG. 4.

(II) Preparation of Cell Strain Expressing Stably After Passages

According to Maniatis et al. method described in "Molecular Cloning", Cold Spring Harbor Laboratory, 86–96 (1982), plasmid pKCRHGF-2 prepared in (I) above, in which two hHGF cDNA fragments had been inserted into the BamHI cleavage site of pKCR (Proc. Natl. Acad. Sci., 78 (2), 1527 (1981)), was recovered from the recombinant *E. coli* and purified to obtain a large amount of HGF expression plasmid DNA.

On the other hand, plasmid pSV2neo DNA (J. Appl. Genet., 1, 327 (1982)) and plasmid pAd-D26-1 DNA (J. Molec. Biol., 159, 601 (1982)), each coding for a marker for selecting transformants, were recovered from recombinant *E. coli* strains containing the respective plasmid and purified, in accordance with the aforementioned Maniatis et al. method.

Three plasmids thus prepared were used to co-transform CHO cells in accordance with Ausubel et al. method described in "Current Protocols in Molecular Biology", Greene Publishing Associates and Wiley-Interscience, Chapters 9.1.1 to 9.1.4, (1987).

First, CHO cells were cultured to semi-confluent in ERDF medium (Kyokuto Seiyaku, Japan) containing 10% FCS (fetal calf serum) in a Petri dish of 9 cm in diameter. The medium was removed from the dish and there was added dropwise a DNA solution, which had previously been prepared in the following manner:

In an Eppendorf centrifugal tube, 300 ml of 2×HEBS solution (1.6% sodium chloride, 0.074% potassium chloride, 0.05% disodium hydrogenphosphate dodecahydrate, 0.2% dextrose, 1% HEPES (pH 7.05)), 10 ug of the expression plasmid DNA, 1 ug of pSV2neo plasmid DNA, and 1 ug of pAd-D26-1 plasmid DNA were added per each Petri dish of 9 cm in diameter and sterilized water added to 570 ul in total volume. To the DNA solution, 30 ul of 2.5 M calcium chloride solution was added dropwise while blending vigorously on a Vortex mixer for a few seconds. The resulting mixture was allowed to stand at room temperature for 30 minutes while mixing by Vortex mixer each 10 minutes.

This DNA solution was added to the semi-confluent cells in Petri dish and the cells were allowed to stand at room temperature for 30 minutes. Then, 9 ml of ERDF medium containing 10% FCS was added to the dish followed by culturing in the presence of 5% $CO_2$ at 37° C. for 4 to 5 hours.

The media was removed from the dish and the cells were washed with 5 ml of 1×TBS++ solution (25 mM Tris-HCl, pH 7.5, 140 mM sodium chloride, 5 mM potassium chloride, 0.6 mM disodium hydrogenphosphate, 0.08 mM calcium chloride, 0.08 mM magnesium chloride). After removing the 1×TBS++ solution, 5 ml of 1×TBS++ solution containing 20% glycerol was added to the cells. The cells were allowed to stand at room temperature for 1 to 2 minutes. After removing the supernatant, the cells were again washed with 5 ml of 1×TBS++ solution. Thereafter, 10 ml of ERDF medium containing 10% FCS was added to the Petri dish followed by culturing in the presence of 5% $CO_2$ at 37° C.

After 48 hours culture, the medium was removed from the dish and the cells were washed with 5 ml of 1×TBS++ solution. Then, 2 ml of trypsin-EDTA solution (Sigma) was added to the cells and the mixture was allowed to stand at room temperature for 30 seconds. The trypsin-EDTA solution was then removed from the dish. After 5 minutes, 10 ml of ERDF medium containing 10% FCS was added to the dish to strip off the cells. The cultured cells of one Petri dish of 9 cm in diameter were divided into 10 portions and each portion was placed in a Petri dish of 9 cm in diameter. G418 sulphate (GENETICIN, GIBCO) was added to each dish to 200 ug/ml and the cells were further cultured.

Ten days later, surviving G418-resistant cells were isolated and distributed in wells of a 24-well culture plate, each well of 3.1 $cm^2$ containing 1 ml of ERDF medium +10% FCS, followed by further culturing for approximately 7 days.

The medium was replaced by FCS-free ERDF medium and the culture was continued for further 72 hours. Then, 2 ml of the medium was recovered from each well and concentrated to 50 ul by Centricon (Millipore). About 15 ul of the sample was subjected to electrophoresis on SDS-polyacrylamide gel.

These samples were analyzed by conventional Western blotting method to confirm the expression of hHGF protein. The presence of the biological activity was also confirmed by measuring hHGF activity according to Gohda et al. method described in Exp. Cell Res., 166, 139–150 (1986).

Further, the cells obtained were isolated from each well and quantitative measurement of hHGF protein was performed by enzyme immunoassay. The amount of hHGF expressed was determined in B-1, B-27 and B-102 cells, which produced a significantly lare amount of protein.

EXAMPLE 3: Preparation of Cell Strain Expressing Stably After Passages by Double Transformation Plasmid DNAs of the expression vector pKCRHGF-2 prepared in (I) above and pMBG coding for mycophenolic acid resistance as a marker for selecting transformants (Nature, 294, 228 (1981)) were recovered from recombinant E. coli strains containing the respective plasmid and purified, in accordance with the aforementioned Maniatis et al. method.

The resulting two plasmids were used to again co-transform each of those cells B-1, B-27 and B-102 which was isolated in Example 2 (II) and capable of expressing a large amount of hHGF stably after passages, in accordance with Ausubel et al. method described in "Current Protocols in Molecular Biology", Greene Publishing Associates and Wiley-Interscience, Chapters 9.1.1 to 9.1.4, (1987).

First, the hHGF-expressing cells were cultured to semi-confluent in ERDF medium containing 10% FCS in a Petri dish of 9 cm in diameter. The medium was then removed from the dish and there was added dropwise the DNA solution, which had previously been prepared in the same manner as in Example 2 (II) except that 10 ug of pKCRHGF-2 plasmid DNA and 1 ug of pMBG plasmid DNA were used.

This DNA solution was added to the semi-confluent cells in Petri dish and the cells were allowed to stand at room temperature for 30 minutes. Then, 9 ml of ERDF medium containing 10% FCS was added to the dish followed by culturing in the presence of 5% $CO_2$ at 37° C. for 4 to 5 hours.

The medium was removed from the dish and the cells were washed with 5 ml of 1×TBS++ solution. After removing the 1×TBS++ solution, 5 ml of 1×TBS++ solution containing 20% glycerol was added to the cells. The cells were allowed to stand at room temperature for 1 to 2 minutes. After removing the supernatant, the cells were again washed with 5 ml of 1×TBS++ solution. Thereafter, 10 ml of ERDF medium containing 10% FCS was added to the Petri dish followed by culturing in the presence of 5% $CO_2$ at 37° C.

After 48 hours culture, the medium was removed from the dish and the cells were washed with 5 ml of 1×TBS++ solution. Then, 2 ml of trypsin-EDTA solution (Sigma) was added to the cells and the mixture was allowed to stand at room temperature for 30 seconds. The trypsin-EDTA solution was then removed from the dish. After 5 minutes, 10 ml of alpha-MEM(–) medium containing 10% FCS was added to the dish to strip off the cells. The cultured cells of one Petri dish of 9 cm in diameter were divided into 10 portions and each portion was placed in a Petri dish of 9 cm in diameter. Mycophenolic acid (Sigma) and xanthine (Sigma) were added to each dish to 1 ug/ml and 250 ug/ml, respectively, and the cells were further cultured.

Ten days later, surviving mycophenolic acid-resistant cells were isolated and distributed in wells of a 24-well culture plate, each well of 3.1 $cm^2$ containing 1 ml of ERDF medium+10% FCS, followed by further culturing for approximately 7 days.

The medium was replaced by FCS-free ERDF medium and the culture was continued for further 72 hours. Then, 2 ml of the medium was recovered from each well and concentrated to 50 ul by Centricon (Millipore). About 15 ul of the sample was subjected to electrophoresis on SDS-polyacrylamide gel.

Figure 5:
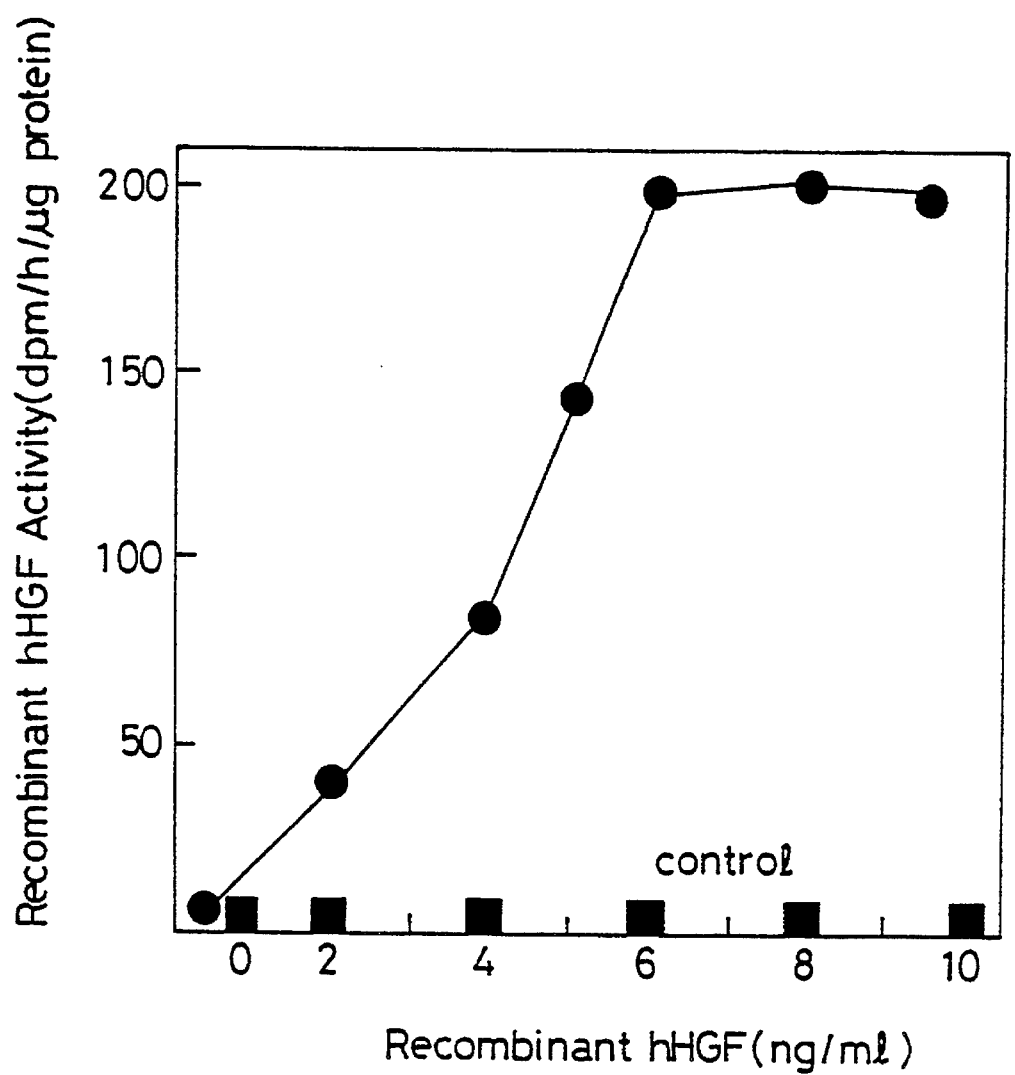
FIG. 5 is a graph showing the biological activity of the supernatant containing human parenchymal cell growth factor produced by CHO cells carrying the expression vector which has the DNA coding for the human parenchymal cell growth factor of the present invention.

These samples were analyzed by conventional Western blotting method to confirm the expression of hHGF protein. The presence of the biological activity was also confirmed by measuring hHGF activity according to Gohda et al. method described in Exp. Cell Res., 166, 139–150 (1986). The results are shown in FIG. 5.

Further, some of the obtained cells were isolated and the amount of hHGF protein expressed was measured by enzyme immunoassay. There was obtained doubly transformed BD-24 cell exhibiting the amount of hHGF expressed, which was 20-fold that of single transformant B-102 cell.

EXAMPLE 4

The hHGF producing cell BD-24 prepared in Example 3 was cultured in ERDF medium containing 10% FCS. The supernatant (500 ml) was adsorbed on a column filled with 10 ml S-Sepharose Fast Flow™ (Pharmacia). The proteins were eluted using 10 mM sodium phosphate-containing buffer (pH 7.5) with increasing concentrations of sodium chloride therein. Recombinant hHGF protein was eluted with approximately 0.7M sodium chloride.

This hHGF fraction was analyzed by SDS-polyacrylamide gel electrophoresis yielding a broad band with molecular weights of about 76,000 to 92,000 under non-reducing condition and on the other hand a broad band of about 60,000 to 65,000 and a weak band of about 56,000 under reducing condition, which corresponded to H chain of hHGF protein, further giving two bands with molecular weights of about 32,000 to 35,000, which corresponded to L chain of hHGF protein. These band multiplicity and broadness may arise from heterogeneity of glycosylated sugar chains on hHGF protein.

The buffer of the purified hHGF protein solution was substitued by 0.1M aqueous ammonium bicarbonate solution. This solution was mixed with 1/50 volume of *Staphylococcus aureus* V8 protease (Miles Laboratory) and incubated at 37° C. overnight to yield a peptide mixture. This mixture was subjected to reverse phase high pressure liquid chromatography using C8 column (Bakerbond, 4.6×250 mm) while increasing acetonitrile concentration from 0% to 60% at a rate of 1% per minute.

Approximately 10 peptide peaks eluted were subjected to amino acid analysis to reveal that the peak eluted at about 18 minutes has the amino acid composition as shown in Table below.

TABLE

| Amino Acid Composition | |
|---|---|
| Aspartic acid/Asparagine | 1.22 |

TABLE-continued

Amino Acid Composition

| | |
|---|---|
| Threonine | 0.63 |
| Glutamic acid/Glutamine | 2.03 |
| Isoleucine | 0.99 |
| Lysine | 0.92 |
| Histidine | 0.65 |
| Arginine | 3.11 |

The composition shown in Table substantially coincides with the theoretical composition of a peptide extending from the 32nd glutamine to the 41st glutamic acid, as calculated from the first methionine, in the amino acid sequence (FIG. 1) deduced from the base sequence of cDNA coding for hHGF (FIG. 2).

This peptide was analyzed by fast atom bombardment massspectroscopy (NIHON DENSHI, Japan, model HX-100). A peak was found at mass 1321 indicating that the peptide had a molecular weight of 1320. Since the theoretical molecular weight of the peptide extending from the 32nd glutamine to the 41st glutamic acid is 1337 of the amino acid sequence shown in FIG. 1, it can be concluded that the amino terminal glutamine of this peptide is converted by deamination into pyroglutamic acid.

Thus, the N terminal amino acid of the secreted hHGF protein is found to be pyroglutamic acid derived from the 32nd amind acid glutamine in the amino acid sequence shown in FIG. 1.

What is claimed is:

1. An isolated gene coding for hepatic parenchymal cell growth factor represented by the following amino acid sequence:

| | | | | | | | | | |
|---|---|---|---|---|---|---|---|---|---|
| Met | Trp | Val | Thr | Lys | Leu | Leu | Pro | Ala | Leu |
| Leu | Leu | Gln | His | Val | Leu | Leu | His | Leu | Leu |
| Leu | Leu | Pro | Ile | Ala | Ile | Pro | Tyr | Ala | Glu |
| Gly | Gln | Arg | Lys | Arg | Arg | Asn | Thr | Ile | His |
| Glu | Phe | Lys | Lys | Ser | Ala | Lys | Thr | Thr | Leu |
| Ile | Lys | Ile | Asp | Pro | Ala | Leu | Lys | Ile | Lys |
| Thr | Lys | Lys | Val | Asn | Thr | Ala | Asp | Gln | Cys |
| Ala | Asn | Arg | Cys | Thr | Arg | Asn | Lys | Gly | Leu |
| Pro | Phe | Thr | Cys | Lys | Ala | Phe | Val | Phe | Asp |
| Lys | Ala | Arg | Lys | Gln | Cys | Leu | Trp | Phe | Pro |
| Phe | Asn | Ser | Met | Ser | Ser | Gly | Val | Lys | Lys |
| Glu | Phe | Gly | His | Glu | Phe | Asp | Leu | Tyr | Glu |
| Asn | Lys | Asp | Tyr | Ile | Arg | Asn | Cys | Ile | Ile |
| Gly | Lys | Gly | Arg | Ser | Tyr | Lys | Gly | Thr | Val |
| Ser | Ile | Thr | Lys | Ser | Gly | Ile | Lys | Cys | Gln |
| Pro | Trp | Ser | Ser | Met | Ile | Pro | His | Glu | His |
| Ser | Phe | Leu | Pro | Ser | Ser | Tyr | Arg | Gly | Lys |
| Asp | Leu | Gln | Glu | Asn | Tyr | Cys | Arg | Asn | Pro |
| Arg | Gly | Glu | Glu | Gly | Gly | Pro | Trp | Cys | Phe |
| Thr | Ser | Asn | Pro | Glu | Val | Arg | Tyr | Glu | Val |
| Cys | Asp | Ile | Pro | Gln | Cys | Ser | Glu | Val | Glu |
| Cys | Met | Thr | Cys | Asn | Gly | Glu | Ser | Tyr | Arg |
| Gly | Leu | Met | Asp | His | Thr | Glu | Ser | Gly | Lys |
| Ile | Cys | Gln | Arg | Trp | Asp | His | Gln | Thr | Pro |
| His | Arg | His | Lys | Phe | Leu | Pro | Glu | Arg | Tyr |
| Pro | Asp | Lys | Gly | Phe | Asp | Asp | Asn | Tyr | Cys |
| Arg | Asn | Pro | Asp | Gly | Gln | Pro | Arg | Pro | Trp |
| Cys | Tyr | Thr | Leu | Asp | Pro | His | Thr | Arg | Trp |
| Glu | Tyr | Cys | Ala | Ile | Lys | Thr | Cys | Ala | Asp |
| Asn | Thr | Met | Asn | Asp | Thr | Asp | Val | Pro | Leu |
| Glu | Thr | Thr | Glu | Cys | Ile | Gln | Gly | Gln | Gly |
| Glu | Gly | Tyr | Arg | Gly | Thr | Val | Asn | Thr | Ile |
| Trp | Asn | Gly | Ile | Pro | Cys | Gln | Arg | Trp | Asp |
| Ser | Gln | Tyr | Pro | His | Glu | His | Asp | Met | Thr |
| Pro | Glu | Asn | Phe | Lys | Cys | Lys | Asp | Leu | Arg |
| Glu | Asn | Tyr | Cys | Arg | Asn | Pro | Asp | Gly | Ser |
| Glu | Ser | Pro | Trp | Cys | Phe | Thr | Thr | Asp | Pro |
| Asn | Ile | Arg | Val | Gly | Tyr | Cys | Ser | Gln | Ile |
| Pro | Asn | Cys | Asp | Met | Ser | His | Gly | Gln | Asp |
| Cys | Tyr | Arg | Gly | Asn | Gly | Lys | Asn | Tyr | Met |
| Gly | Asn | Leu | Ser | Gln | Thr | Arg | Ser | Gly | Leu |
| Thr | Cys | Ser | Met | Trp | Asp | Lys | Asn | Met | Glu |
| Asp | Leu | His | Arg | His | Ile | Phe | Trp | Glu | Pro |
| Asp | Ala | Ser | Lys | Leu | Asn | Glu | Asn | Tyr | Cys |
| Arg | Asn | Pro | Asp | Asp | Asp | Ala | His | Gly | Pro |
| Trp | Cys | Tyr | Thr | Gly | Asn | Pro | Leu | Ile | Pro |
| Trp | Asp | Tyr | Cys | Pro | Ile | Ser | Arg | Cys | Glu |
| Gly | Asp | Thr | Thr | Pro | Thr | Ile | Val | Asn | Leu |
| Asp | His | Pro | Val | Ile | Ser | Cys | Ala | Lys | Thr |
| Lys | Gln | Leu | Arg | Val | Val | Asn | Gly | Ile | Pro |
| Thr | Arg | Thr | Asn | Ile | Gly | Trp | Met | Val | Ser |
| Leu | Arg | Tyr | Arg | Asn | Lys | His | Ile | Cys | Gly |
| Gly | Ser | Leu | Ile | Lys | Glu | Ser | Trp | Val | Leu |
| Thr | Ala | Arg | Gln | Cys | Phe | Pro | Ser | Arg | Asp |
| Leu | Lys | Asp | Tyr | Glu | Ala | Trp | Leu | Gly | Ile |
| His | Asp | Val | His | Gly | Arg | Gly | Asp | Glu | Lys |
| Cys | Lys | Gln | Val | Leu | Asn | Val | Ser | Gln | Leu |
| Val | Tyr | Gly | Pro | Glu | Gly | Ser | Asp | Leu | Val |
| Leu | Met | Lys | Leu | Ala | Arg | Pro | Ala | Val | Leu |
| Asp | Asp | Phe | Val | Ser | Thr | Ile | Asp | Leu | Pro |
| Asn | Tyr | Gly | Cys | Thr | Ile | Pro | Glu | Lys | Thr |
| Ser | Cys | Ser | Val | Tyr | Gly | Trp | Gly | Tyr | Thr |
| Gly | Leu | Ile | Asn | Tyr | Asp | Gly | Leu | Leu | Arg |
| Val | Ala | His | Leu | Tyr | Ile | Met | Gly | Asn | Glu |
| Lys | Cys | Ser | Gln | His | His | Arg | Gly | Lys | Val |
| Thr | Leu | Asn | Glu | Ser | Glu | Ile | Cys | Ala | Gly |
| Ala | Glu | Lys | Ile | Gly | Ser | Gly | Pro | Cys | Glu |
| Gly | Asp | Tyr | Gly | Gly | Pro | Leu | Val | Cys | Glu |
| Gln | His | Lys | Met | Arg | Met | Val | Leu | Gly | Val |
| Ile | Val | Pro | Gly | Arg | Gly | Cys | Ala | Ile | Pro |
| Asn | Arg | Pro | Gly | Ile | Phe | Val | Arg | Val | Ala |
| Tyr | Tyr | Ala | Lys | Trp | Ile | His | Lys | Ile | Ile |
| Leu | Thr | Tyr | Lys | Val | Pro | Gln | Ser | * | |

2. An isolated gene coding for hepatic parenchymal cell growth factor represented by the following amino acid sequence:

| | | | | | | | | | |
|---|---|---|---|---|---|---|---|---|---|
| | | | | | | | | | Glu |
| Gly | Gln | Arg | Lys | Arg | Arg | Asn | Thr | Ile | His |
| Glu | Phe | Lys | Lys | Ser | Ala | Lys | Thr | Thr | Leu |
| Ile | Lys | Ile | Asp | Pro | Ala | Leu | Lys | Ile | Lys |
| Thr | Lys | Lys | Val | Asn | Thr | Ala | Asp | Gln | Cys |
| Ala | Asn | Arg | Cys | Thr | Arg | Asn | Lys | Gly | Leu |
| Pro | Phe | Thr | Cys | Lys | Ala | Phe | Val | Phe | Asp |
| Lys | Ala | Arg | Lys | Gln | Cys | Leu | Trp | Phe | Pro |
| Phe | Asn | Ser | Met | Ser | Ser | Gly | Val | Lys | Lys |
| Glu | Phe | Gly | His | Glu | Phe | Asp | Leu | Tyr | Glu |
| Asn | Lys | Asp | Tyr | Ile | Arg | Asn | Cys | Ile | Ile |
| Gly | Lys | Gly | Arg | Ser | Tyr | Lys | Gly | Thr | Val |
| Ser | Ile | Thr | Lys | Ser | Gly | Ile | Lys | Cys | Gln |
| Pro | Trp | Ser | Ser | Met | Ile | Pro | His | Glu | His |
| Ser | Phe | Leu | Pro | Ser | Ser | Tyr | Arg | Gly | Lys |
| Asp | Leu | Gln | Glu | Asn | Tyr | Cys | Arg | Asn | Pro |
| Arg | Gly | Glu | Glu | Gly | Gly | Pro | Trp | Cys | Phe |
| Thr | Ser | Asn | Pro | Glu | Val | Arg | Tyr | Glu | Val |
| Cys | Asp | Ile | Pro | Gln | Cys | Ser | Glu | Val | Glu |
| Cys | Met | Thr | Cys | Asn | Gly | Glu | Ser | Tyr | Arg |
| Gly | Leu | Met | Asp | His | Thr | Glu | Ser | Gly | Lys |
| Ile | Cys | Gln | Arg | Trp | Asp | His | Gln | Thr | Pro |
| His | Arg | His | Lys | Phe | Leu | Pro | Glu | Arg | Tyr |
| Pro | Asp | Lys | Gly | Phe | Asp | Asp | Asn | Tyr | Cys |
| Arg | Asn | Pro | Asp | Gly | Gln | Pro | Arg | Pro | Trp |
| Cys | Tyr | Thr | Leu | Asp | Pro | His | Thr | Arg | Trp |
| Glu | Tyr | Cys | Ala | Ile | Lys | Thr | Cys | Ala | Asp |
| Asn | Thr | Met | Asn | Asp | Thr | Asp | Val | Pro | Leu |
| Glu | Thr | Thr | Glu | Cys | Ile | Gln | Gly | Gln | Gly |
| Glu | Gly | Tyr | Arg | Gly | Thr | Val | Asn | Thr | Ile |
| Trp | Asn | Gly | Ile | Pro | Cys | Gln | Arg | Trp | Asp |
| Ser | Gln | Tyr | Pro | His | Glu | His | Asp | Met | Thr |
| Pro | Glu | Asn | Phe | Lys | Cys | Lys | Asp | Leu | Arg |
| Glu | Asn | Tyr | Cys | Arg | Asn | Pro | Asp | Gly | Ser |
| Glu | Ser | Pro | Trp | Cys | Phe | Thr | Thr | Asp | Pro |
| Asn | Ile | Arg | Val | Gly | Tyr | Cys | Ser | Gln | Ile |
| Pro | Asn | Cys | Asp | Met | Ser | His | Gly | Gln | Asp |
| Cys | Tyr | Arg | Gly | Asn | Gly | Lys | Asn | Tyr | Met |

-continued

| | | | | | | | | | |
|---|---|---|---|---|---|---|---|---|---|
| Gly | Asn | Leu | Ser | Gln | Thr | Arg | Ser | Gly | Leu |
| Thr | Cys | Ser | Met | Trp | Asp | Lys | Asn | Met | Glu |
| Asp | Leu | His | Arg | His | Ile | Phe | Trp | Glu | Pro |
| Asp | Ala | Ser | Lys | Leu | Asn | Glu | Asn | Tyr | Cys |
| Arg | Asn | Pro | Asp | Asp | Asp | Ala | His | Gly | Pro |
| Trp | Cys | Tyr | Thr | Gly | Asn | Pro | Leu | Ile | Pro |
| Trp | Asp | Tyr | Cys | Pro | Ile | Ser | Arg | Cys | Glu |
| Gly | Asp | Thr | Thr | Pro | Thr | Ile | Val | Asn | Leu |
| Asp | His | Pro | Val | Ile | Ser | Cys | Ala | Lys | Thr |
| Lys | Gln | Leu | Arg | Val | Val | Asn | Gly | Ile | Pro |
| Thr | Arg | Thr | Asn | Ile | Gly | Trp | Met | Val | Ser |
| Leu | Arg | Tyr | Arg | Asn | Lys | His | Ile | Cys | Gly |
| Gly | Ser | Leu | Ile | Lys | Glu | Ser | Trp | Val | Leu |
| Thr | Ala | Arg | Gln | Cys | Phe | Pro | Ser | Arg | Asp |
| Leu | Lys | Asp | Tyr | Glu | Ala | Trp | Leu | Gly | Ile |
| His | Asp | Val | His | Gly | Arg | Gly | Asp | Glu | Lys |
| Cys | Lys | Gln | Val | Leu | Asn | Val | Ser | Gln | Leu |
| Val | Tyr | Gly | Pro | Glu | Gly | Ser | Asp | Leu | Val |
| Leu | Met | Lys | Leu | Ala | Arg | Pro | Ala | Val | Leu |
| Asp | Asp | Phe | Val | Ser | Thr | Ile | Asp | Leu | Pro |
| Asn | Tyr | Gly | Cys | Thr | Ile | Pro | Glu | Lys | Thr |
| Ser | Cys | Ser | Val | Tyr | Gly | Trp | Gly | Tyr | Thr |
| Gly | Leu | Ile | Asn | Tyr | Asp | Gly | Leu | Leu | Arg |
| Val | Ala | His | Leu | Tyr | Ile | Met | Gly | Asn | Glu |
| Lys | Cys | Ser | Gln | His | His | Arg | Gly | Lys | Val |
| Thr | Leu | Asn | Glu | Ser | Glu | Ile | Cys | Ala | Gly |
| Ala | Glu | Lys | Ile | Gly | Ser | Gly | Pro | Cys | Glu |
| Gly | Asp | Tyr | Gly | Gly | Pro | Leu | Val | Cys | Glu |
| Gln | His | Lys | Met | Arg | Met | Val | Leu | Gly | Val |
| Ile | Val | Pro | Gly | Arg | Gly | Cys | Ala | Ile | Pro |
| Asn | Arg | Pro | Gly | Ile | Phe | Val | Arg | Val | Ala |
| Tyr | Tyr | Ala | Lys | Trp | Ile | His | Lys | Ile | Ile |
| Leu | Thr | Tyr | Lys | Val | Pro | Gln | Ser | * | |

3. An isolated gene coding for hepatic parenchymal cell growth factor represented by the following amino acid sequence:

| | | | | | | | | | |
|---|---|---|---|---|---|---|---|---|---|
| | Gln | Arg | Lys | Arg | Arg | Asn | Thr | Ile | His |
| Glu | Phe | Lys | Lys | Ser | Ala | Lys | Thr | Thr | Leu |
| Ile | Lys | Ile | Asp | Pro | Ala | Leu | Lys | Ile | Lys |
| Thr | Lys | Lys | Val | Asn | Thr | Ala | Asp | Gln | Cys |
| Ala | Asn | Arg | Cys | Thr | Arg | Asn | Lys | Gly | Leu |
| Pro | Phe | Thr | Cys | Lys | Ala | Phe | Val | Phe | Asp |
| Lys | Ala | Arg | Lys | Gln | Cys | Leu | Trp | Phe | Pro |
| Phe | Asn | Ser | Met | Ser | Ser | Gly | Val | Lys | Lys |
| Glu | Phe | Gly | His | Glu | Phe | Asp | Leu | Tyr | Glu |
| Asn | Lys | Asp | Tyr | Ile | Arg | Asn | Cys | Ile | Ile |
| Gly | Lys | Gly | Arg | Ser | Tyr | Lys | Gly | Thr | Val |
| Ser | Ile | Thr | Lys | Ser | Gly | Ile | Lys | Cys | Gln |
| Pro | Trp | Ser | Ser | Met | Ile | Pro | His | Glu | His |
| Ser | Phe | Leu | Pro | Ser | Ser | Tyr | Arg | Gly | Lys |
| Asp | Leu | Gln | Glu | Asn | Tyr | Cys | Arg | Asn | Pro |
| Arg | Gly | Glu | Glu | Gly | Gly | Pro | Trp | Cys | Phe |
| Thr | Ser | Asn | Pro | Glu | Val | Arg | Tyr | Glu | Val |
| Cys | Asp | Ile | Pro | Gln | Cys | Ser | Glu | Val | Glu |
| Cys | Met | Thr | Cys | Asn | Gly | Glu | Ser | Tyr | Arg |
| Gly | Leu | Met | Asp | His | Thr | Glu | Ser | Gly | Lys |
| Ile | Cys | Gln | Arg | Trp | Asp | His | Gln | Thr | Pro |
| His | Arg | His | Lys | Phe | Leu | Pro | Glu | Arg | Tyr |
| Pro | Asp | Lys | Gly | Phe | Asp | Asp | Asn | Tyr | Cys |
| Arg | Asn | Pro | Asp | Gly | Gln | Pro | Arg | Pro | Trp |
| Cys | Tyr | Thr | Leu | Asp | Pro | His | Thr | Arg | Trp |
| Glu | Tyr | Cys | Ala | Ile | Lys | Thr | Cys | Ala | Asp |
| Asn | Thr | Met | Asn | Asp | Thr | Asp | Val | Pro | Leu |
| Glu | Thr | Thr | Glu | Cys | Ile | Gln | Gly | Gln | Gly |
| Glu | Gly | Tyr | Arg | Gly | Thr | Val | Asn | Thr | Ile |
| Trp | Asn | Gly | Ile | Pro | Cys | Gln | Arg | Trp | Asp |
| Ser | Gln | Tyr | Pro | His | Glu | His | Asp | Met | Thr |
| Pro | Glu | Asn | Phe | Lys | Cys | Lys | Asp | Leu | Arg |
| Glu | Asn | Tyr | Cys | Arg | Asn | Pro | Asp | Gly | Ser |
| Glu | Ser | Pro | Trp | Cys | Phe | Thr | Thr | Asp | Pro |
| Asn | Ile | Arg | Val | Gly | Tyr | Cys | Ser | Gln | Ile |
| Pro | Asn | Cys | Asp | Met | Ser | His | Gly | Gln | Asp |
| Cys | Tyr | Arg | Gly | Asn | Gly | Lys | Asn | Tyr | Met |
| Gly | Asn | Leu | Ser | Gln | Thr | Arg | Ser | Gly | Leu |
| Thr | Cys | Ser | Met | Trp | Asp | Lys | Asn | Met | Glu |
| Asp | Leu | His | Arg | His | Ile | Phe | Trp | Glu | Pro |
| Asp | Ala | Ser | Lys | Leu | Asn | Glu | Asn | Tyr | Cys |
| Arg | Asn | Pro | Asp | Ala | Asp | Ala | His | Gly | Pro |
| Trp | Cys | Tyr | Thr | Gly | Asn | Pro | Leu | Ile | Pro |
| Trp | Asp | Tyr | Cys | Pro | Ile | Ser | Arg | Cys | Glu |
| Gly | Asp | Thr | Thr | Pro | Thr | Ile | Val | Asn | Leu |
| Asp | His | Pro | Val | Ile | Ser | Cys | Ala | Lys | Thr |
| Lys | Gln | Leu | Arg | Val | Val | Asn | Gly | Ile | Pro |
| Thr | Arg | Thr | Asn | Ile | Gly | Trp | Met | Val | Ser |
| Leu | Arg | Tyr | Arg | Asn | Lys | His | Ile | Cys | Gly |
| Gly | Ser | Leu | Ile | Lys | Glu | Ser | Trp | Val | Leu |
| Thr | Ala | Arg | Gln | Cys | Phe | Pro | Ser | Arg | Asp |
| Leu | Lys | Asp | Tyr | Glu | Ala | Trp | Leu | Gly | Ile |
| His | Asp | Val | His | Gly | Arg | Gly | Asp | Glu | Lys |
| Cys | Lys | Gln | Val | Leu | Asn | Val | Ser | Gln | Leu |
| Val | Tyr | Gly | Pro | Glu | Gly | Ser | Asp | Leu | Val |
| Leu | Met | Lys | Leu | Ala | Arg | Pro | Ala | Val | Leu |
| Asp | Asp | Phe | Val | Ser | Thr | Ile | Asp | Leu | Pro |
| Asn | Tyr | Gly | Cys | Thr | Ile | Pro | Glu | Lys | Thr |
| Ser | Cys | Ser | Val | Tyr | Gly | Trp | Gly | Tyr | Thr |
| Gly | Leu | Ile | Asn | Tyr | Asp | Gly | Leu | Leu | Arg |
| Val | Ala | His | Leu | Tyr | Ile | Met | Gly | Asn | Glu |
| Lys | Cys | Ser | Gln | His | His | Arg | Gly | Lys | Val |
| Thr | Leu | Asn | Glu | Ser | Glu | Ile | Cys | Ala | Gly |
| Ala | Glu | Lys | Ile | Gly | Ser | Gly | Pro | Cys | Glu |
| Gly | Asp | Tyr | Gly | Gly | Pro | Leu | Val | Cys | Glu |
| Gln | His | Lys | Met | Arg | Met | Val | Leu | Gly | Val |
| Ile | Val | Pro | Gly | Arg | Gly | Cys | Ala | Ile | Pro |
| Asn | Arg | Pro | Gly | Ile | Phe | Val | Arg | Val | Ala |
| Tyr | Tyr | Ala | Lys | Trp | Ile | His | Lys | Ile | Ile |
| Leu | Thr | Tyr | Lys | Val | Pro | Gln | Ser | * | |

4. The isolated gene coding for hepatic parenchymal cell growth factor, which is represented by the following base sequence:

| | | | | | | | | | |
|---|---|---|---|---|---|---|---|---|---|
| ATG | TGG | GTG | ACC | AAA | CTC | CTG | CCA | GCC | CTG |
| CTG | CTG | CAG | CAT | GTC | CTC | CTG | CAT | CTC | CTC |
| CTG | CTC | CCC | ATC | GCC | ATC | CCC | TAT | GCA | GAG |
| GGA | CAA | AGG | AAA | AGA | AGA | AAT | ACA | ATT | CAT |
| GAA | TTC | AAA | AAA | TCA | GCA | AAG | ACT | ACC | CTA |
| ATC | AAA | ATA | GAT | CCA | GCA | CTG | AAG | ATA | AAA |
| ACC | AAA | AAA | GTG | AAT | ACT | GCA | GAC | CAA | TGT |
| GCT | AAT | AGA | TGT | ACT | AGG | AAT | AAA | GGA | CTT |
| CCA | TTC | ACT | TGC | AAG | GCT | TTT | GTT | TTT | GAT |
| AAA | GCA | AGA | AAA | CAA | TGC | CTC | TGG | TTC | CCC |
| TTC | AAT | AGC | ATG | TCA | AGT | GGA | GTG | AAA | AAA |
| GAA | TTT | GGC | CAT | GAA | TTT | GAC | CTC | TAT | GAA |
| AAC | AAA | GAC | TAC | ATT | AGA | AAC | TGC | ATC | ATT |
| GGT | AAA | GGA | CGC | ACG | TAC | AAG | GGA | ACA | GTA |
| TCT | ATC | ACT | AAG | AGT | GGC | ATC | AAA | TGT | CAG |
| CCC | TGG | AGT | TCC | ATG | ATA | CCA | CAC | GAA | CAC |
| AGC | TTT | TTG | CCT | TCG | AGC | TAT | CGG | GGT | AAA |
| GAC | CTA | CAG | GAA | AAC | TAC | TGT | CGA | AAT | CCT |

-continued

| | | | | | | | | |
|---|---|---|---|---|---|---|---|---|
| CGA | GGG | GAA | GAA | GGG | GGA | CCC | TGG | TGT | TTC |
| ACA | AGC | AAT | CCA | GAG | GTA | CGC | TAC | GAA | GTC |
| TGT | GAC | ATT | CCT | CAG | TGT | TCA | GAA | GTT | GAA |
| TGC | ATG | ACC | TGC | AAT | GGG | GAG | AGT | TAT | CGA |
| GGT | CTC | ATG | GAT | CAT | ACA | GAA | TCA | GGC | AAG |
| ATT | TGT | CAG | CGC | TGG | GAT | CAT | CAG | ACA | CCA |
| CAC | CGG | CAC | AAA | TTC | TTG | CCT | GAA | AGA | TAT |
| CCC | GAC | AAG | GGC | TTT | GAT | GAT | AAT | TAT | TGC |
| CGC | AAT | CCC | GAT | GGC | CAG | CCG | AGG | CCA | TGG |
| TGC | TAT | ACT | CTT | GAC | CCT | CAC | ACC | CGC | TGG |
| GAG | TAC | TGT | GCA | ATT | AAA | ACA | TGC | GCT | GAC |
| AAT | ACT | ATG | AAT | GAC | ACT | GAT | GTT | CCT | TTG |
| GAA | ACA | ACT | GAA | TGC | ATC | CAA | GGT | CAA | GGA |
| GAA | GGC | TAC | AGG | GGC | ACT | GTC | AAT | ACC | ATT |
| TGG | AAT | GGA | ATT | CCA | TGT | CAG | CGT | TGG | GAT |
| TCT | CAG | TAT | CCT | CAC | GAG | CAT | GAC | ATG | ACT |
| CCT | GAA | AAT | TTC | AAG | TGC | AAG | GAC | CTA | CGA |
| GAA | AAT | TAC | TGC | CGA | AAT | CCA | GAT | ·GGG | TCT |
| GAA | TCA | CCC | TGG | TGT | TTT | ACC | ACT | CCA | CCA |
| AAC | ATC | CGA | GTT | GGC | TAC | TGC | TCC | CAA | ATT |
| CCA | AAC | TGT | GAT | ATG | TCA | CAT | GGA | CAA | GAT |
| TGT | TAT | CGT | GGG | AAT | GGC | AAA | AAT | TAT | ATG |
| GGC | AAC | TTA | TCC | CAA | ACA | AGA | TCT | GGA | CTA |
| ACA | TGT | TCA | ATG | TGG | GAC | AAG | AAC | ATG | GAA |
| GAC | TTA | CAT | CGT | CAT | ATC | TTC | TGG | GAA | CCA |
| GAT | GCA | AGT | AAG | CTG | AAT | GAG | AAT | TAC | TGC |
| CGA | AAT | CCA | GAT | GAT | GAT | GCT | CAT | GGA | CCC |
| TGG | TGC | TAC | ACG | GGA | AAT | CCA | CTC | ATT | CCT |
| TGG | GAT | TAT | TGC | CCT | ATT | TCT | CGT | TGT | GAA |
| GGT | GAT | ACC | ACA | CCT | ACA | ATA | GTC | AAT | TTA |
| GAC | CAT | CCC | GTA | ATA | TCT | TGT | GCC | AAA | ACG |
| AAA | CAA | TTG | CGA | GTT | GTA | AAT | GGG | ATT | CCA |
| ACA | CGA | ACA | AAC | ATA | GGA | TGG | ATG | GTT | AGT |
| TTG | AGA | TAC | AGA | AAT | AAA | CAT | ATC | TGC | GGA |
| GGA | TCA | TTG | ATA | AAG | GAG | AGT | TGG | GTT | CTT |
| ACT | GCA | CGA | CAG | TGT | TTC | CCT | TCT | CGA | GAC |
| TTG | AAA | GAT | TAT | GAA | GCT | TGG | CTT | GGA | ATT |
| CAT | GAT | GTC | CAC | GGA | AGA | GGA | GAT | GAG | AAA |
| TGC | AAA | CAG | GTT | CTC | AAT | GTT | TCC | CAG | CTG |
| GTA | TAT | GGC | CCT | GAA | GGA | TCA | GAT | CTG | GTT |
| TTA | ATG | AAG | CTT | GCC | AGG | CCT | GCT | GTC | CTG |
| GAT | GAT | TTT | GTT | AGT | ACG | ATT | GAT | TTA | CCT |
| AAT | TAT | GGA | TGC | ACA | ATT | CCT | GAA | AAG | ACC |
| AGT | AGC | AGT | GTT | TAT | GGC | TGG | GGC | TAC | ACT |
| GGA | TTG | ATC | AAC | TAT | GAT | GGC | CTA | TTA | CGA |
| GTG | GCA | CAT | CTC | TAT | ATA | ATG | GGA | AAT | GAG |
| AAA | TGC | AGC | CAG | CAT | CAT | CGA | GGG | AAG | GTG |
| ACT | CTG | AAT | GAG | TCT | GAA | ATA | TGT | GCT | GGG |
| GCT | GAA | AAG | ATT | GGA | TCA | GGA | CCA | TGT | GAG |
| GGG | GAT | TAT | GGT | GGC | CCA | CTT | GTT | TGT | GAG |
| CAA | CAT | AAA | ATG | AGA | ATG | GTT | CTT | GGT | GTC |
| ATT | GTT | CCT | GGT | CGT | GGA | TGT | GCC | ATT | CCA |
| AAT | CGT | CCT | GGT | ATT | TTT | GTC | CGA | GTA | GCA |
| TAT | TAT | GCA | AAA | TGG | ATA | CAC | AAA | ATT | ATT |
| TTA | ACA | TAT | AAG | GTA | CCA | CAG | TCA | TAG | |

5. The isolated gene coding for hepatic parenchymal cell growth factor, which is represented by the following base sequence extending from the 88th base in the sequence which is guanine to the last guanine in the sequence defined in claim 4:

| | | | | | | | | |
|---|---|---|---|---|---|---|---|---|
| | | | | | | | | GAG |
| GGA | CAA | AGG | AAA | AGA | AGA | AAT | ACA | ATT | CAT |
| GAA | TTC | AAA | AAA | TCA | GCA | AAG | ACT | ACC | CTA |
| ATC | AAA | ATA | GAT | CCA | GCA | CTG | AAG | ATA | AAA |
| ACC | AAA | AAA | GTG | AAT | ACT | GCA | GAC | CAA | TGT |
| GCT | AAT | AGA | TGT | ACT | AGG | AAT | AAA | GGA | CTT |
| CCA | TTC | ACT | TGC | AAG | GCT | TTT | GTT | TTT | GAT |
| AAA | GCA | AGA | AAA | CAA | TGC | CTC | TGG | TTC | CCC |
| TTC | AAT | AGC | ATG | TCA | AGT | GGA | GTG | AAA | AAA |
| GAA | TTT | GGC | CAT | GAA | TTT | GAC | CTC | TAT | GAA |
| AAC | AAA | GAC | TAC | ATT | AGA | AAC | TGC | ATC | ATT |
| GGT | AAA | GGA | CGC | ACG | TAC | AAG | GGA | ACA | GTA |
| TCT | ATC | ACT | AAG | AGT | GGC | ATC | AAA | TGT | CAG |
| CCC | TGG | AGT | TCC | ATG | ATA | CCA | CAC | GAA | CAC |
| AGC | TTT | TTG | CCT | TCG | AGC | TAT | CGG | GGT | AAA |
| GAC | CTA | CAG | GAA | AAC | TAC | TGT | CGA | AAT | CCT |

-continued

| | | | | | | | | | |
|---|---|---|---|---|---|---|---|---|---|
| CGA | GGG | GAA | GAA | GGG | GGA | CCC | TGG | TGT | TTC |
| ACA | AGC | AAT | CCA | GAG | GTA | TAC | GAA | GTC | |
| TGT | GAC | ATT | CCT | CAG | TGT | TCA | GAA | GTT | GAA |
| TGC | ATG | ACC | TGC | AAT | GGG | GAG | AGT | TAT | CGA |
| GGT | CTC | ATG | GAT | CAT | ACA | GAA | TCA | GGC | AAG |
| ATT | TGT | CAG | CGC | TGG | GAT | CAT | CAG | ACA | CCA |
| CAC | CGG | CAC | AAA | TTC | TTG | CCT | GAA | AGA | TAT |
| CCC | GAC | AAG | GGC | TTT | GAT | GAT | AAT | TAT | TGC |
| CGC | AAT | CCC | GAT | GGC | CAG | CCG | AGG | CCA | TGG |
| TGC | TAT | ACT | CTT | GAC | CCT | CAC | ACC | CGC | TGG |
| GAG | TAC | TGT | GCA | ATT | AAA | ACA | TGC | GCT | GAC |
| AAT | ACT | ATG | AAT | GAC | ACT | GAT | GTT | CCT | TTG |
| GAA | ACA | ACT | GAA | TGC | ATC | CAA | GGT | CAA | GGA |
| GAA | GGC | TAC | AGG | GGC | ACT | GTC | AAT | ACC | ATT |
| TGG | AAT | GGA | ATT | CCA | TGT | CAG | CGT | TGG | GAT |
| TCT | CAG | TAT | CCT | CAC | GAG | CAT | GAC | ATG | ACT |
| CCT | GAA | AAT | TTC | AAG | TGC | AAG | GAC | CTA | CGA |
| GAA | AAT | TAC | TGC | CGA | AAT | CCA | GAT | GGG | TCT |
| GAA | TCA | CCC | TGG | TGT | TTT | ACC | ACT | GAT | CCA |
| AAC | ATC | CGA | GTT | GGC | TAC | TGC | TCC | CAA | ATT |
| CCA | AAC | TGT | GAT | ATG | TCA | CAT | GGA | CAA | GAT |
| TGT | TAT | CGT | GGG | AAT | GGC | AAA | AAT | TAT | ATG |
| GGC | AAC | TTA | TCC | CAA | ACA | AGA | TCT | GGA | CTA |
| ACA | TGT | TCA | ATG | TGG | GAC | AAG | AAC | ATG | GAA |
| GAC | TTA | CAT | CGT | CAT | ATC | TTC | TGG | GAA | CCA |
| GAT | GCA | AGT | AAG | CTG | AAT | GAG | AAT | TAC | TGC |
| CGA | AAT | CCA | GAT | GAT | GAT | GCT | CAT | GGA | CCC |
| TGG | TGC | TAC | ACG | GGA | AAT | CCA | CTC | ATT | CCT |
| TGG | GAT | TAT | TGC | CCT | ATT | TCT | CGT | TGT | GAA |
| GGT | GAT | ACC | ACA | CCT | ACA | ATA | GTC | AAT | TTA |
| GAC | CAT | CCC | GTA | ATA | TCT | TGT | GCC | AAA | ACG |
| AAA | CAA | TTG | CGA | GTT | GTA | AAT | GGG | ATT | CCA |
| ACA | CGA | ACA | AAC | ATA | GGA | TGG | ATG | GTT | AGT |
| TTG | AGA | TAC | AGA | AAT | AAA | CAT | ATC | TGC | GGA |
| GGA | TCA | TTG | ATA | AAG | GAG | AGT | TGG | GTT | CTT |
| ACT | GCA | CGA | CAG | TGT | TTC | CCT | TCT | CGA | GAC |
| TTG | AAA | GAT | TAT | GAA | GCT | TGG | CTT | GGA | ATT |
| CAT | GAT | GTC | CAC | GGA | AGA | GGA | GAT | GAG | AAA |
| TGC | AAA | CAG | GTT | CTC | AAT | GTT | TCC | CAG | CTG |
| GTA | TAT | GGC | CCT | GAA | GGA | TCA | GAT | CTG | GTT |
| TTA | ATG | AAG | CTT | GCC | AGG | CCT | GCT | GTC | CTG |
| GAT | GAT | TTT | GTT | AGT | ACG | ATT | GAT | TTA | CCT |
| AAT | TAT | GGA | TGC | ACA | ATT | CCT | GAA | AAG | ACC |
| AGT | AGC | AGT | GTT | TAT | GGC | TGG | GGC | TAC | ACT |
| GGA | TTG | ATC | AAC | TAT | GAT | GGC | CTA | TTA | CGA |
| GTG | GCA | CAT | CTC | TAT | ATA | ATG | GGA | AAT | GAG |
| AAA | TGC | AGC | CAG | CAT | CAT | CGA | GGG | AAG | GTG |
| ACT | CTG | AAT | GAG | TCT | GAA | ATA | TGT | GCT | GGG |
| GCT | GAA | AAG | ATT | GGA | TCA | GGA | CCA | TGT | GAG |
| GGG | GAT | TAT | GGT | GGC | CCA | CTT | GTT | TGT | GAG |
| CAA | CAT | AAA | ATG | AGA | ATG | GTT | CTT | GGT | GTC |
| ATT | GTT | CCT | GGT | CGT | GGA | TGT | GCC | ATT | CCA |
| AAT | CGT | CCT | GGT | ATT | TTT | GTC | CGA | GTA | GCA |
| TAT | TAT | GCA | AAA | TGG | ATA | CAC | AAA | ATT | ATT |
| TTA | ACA | TAT | AAG | GTA | CCA | CAG | TCA | TAG | |

6. The isolated gene coding for hepatic parenchymal cell growth factor, which is represented by the following base sequence extending from the 94th base in the sequence which is cytosine to the last guanine in the sequence defined in claim 4:

| | | | | | | | | | |
|---|---|---|---|---|---|---|---|---|---|
| | | CAA | AGG | AAA | AGA | AGA | AAT | ACA | ATT | CAT |
| GAA | TTC | AAA | AAA | TCA | GCA | AAG | ACT | ACC | CTA |
| ATC | AAA | ATA | GAT | CCA | GCA | CTG | AAG | ATA | AAA |
| ACC | AAA | AAA | GTG | AAT | ACT | GCA | GAC | CAA | TGT |
| GCT | AAT | AGA | TGT | ACT | AGG | AAT | AAA | GGA | CTT |
| CCA | TTC | ACT | TGC | AAG | GCT | TTT | GTT | TTT | GAT |
| AAA | GCA | AGA | AAA | CAA | TGC | CTC | TGG | TTC | CCC |
| TTC | AAT | AGC | ATG | TCA | AGT | GGA | GTG | AAA | AAA |
| GAA | TTT | GGC | CAT | GAA | TTT | GAC | CTC | TAT | GAA |
| AAC | AAA | GAC | TAC | ATT | AGA | AAC | TGC | ATC | ATT |
| GGT | AAA | GGA | CGC | ACG | TAC | AAG | GGA | ACA | GTA |
| TCT | ATC | ACT | AAG | AGT | GGC | ATC | AAA | TGT | CAG |
| CCC | TGG | AGT | TCC | ATG | ATA | CCA | CAC | GAA | CAC |
| AGC | TTT | TTG | CCT | TCG | AGC | TAT | CGG | GGT | AAA |
| GAC | CTA | CAG | GAA | AAC | TAC | TGT | CGA | AAT | CCT |
| CGA | GGG | GAA | GAA | GGG | GGA | CCC | TGG | TGT | TTC |

```
ACA  AGC  AAT  CCA  GAG  GTA  CGC  TAC  GAA  GTC
TGT  GAC  ATT  CCT  CAG  TGT  TCA  GAA  GTT  GAA
TGC  ATG  ACC  TGC  AAT  GGG  GAG  AGT  TAT  CGA
GGT  CTC  ATG  GAT  CAT  ACA  GAA  TCA  GGC  AAG
ATT  TGT  CAG  CGC  TGG  GAT  CAT  CAG  ACA  CCA
CAC  CGG  CAC  AAA  TTC  TTG  CCT  GAA  AGA  TAT
CCC  GAC  AAG  GGC  TTT  GAT  GAT  AAT  TAT  TGC
CGC  AAT  CCC  GAT  GGC  CAG  CCG  AGG  CCA  TGG
TGC  TAT  ACT  CTT  GAC  CCT  CAC  ACC  CGC  TGG
GAG  TAC  TGT  GCA  ATT  AAA  ACA  TGC  GCT  GAC
AAT  ACT  ATG  AAT  GAC  ACT  GAT  GTT  CCT  TTG
GAA  ACA  ACT  GAA  TGC  ATC  CAA  GGT  CAA  GGA
GAA  GGC  TAC  AGG  GGC  ACT  GTC  AAT  ACC  ATT
TGG  AAT  GGA  ATT  CCA  TGT  CAG  CGT  TGG  GAT
TCT  CAG  TAT  CCT  CAC  GAG  CAT  GAC  ATG  ACT
CCT  GAA  AAT  TTC  AAG  TGC  AAG  GAC  CTA  CGA
GAA  AAT  TAC  TGC  CGA  AAT  CCA  GAT  GGG  TCT
GAA  TCA  CCC  TGG  TGT  TTT  ACC  ACT  GAT  CCA
AAC  ATC  CGA  GTT  GGC  TAC  TGC  TCC  CAA  ATT
CCA  AAC  TGT  GAT  ATG  TCA  CAT  GGA  CAA  GAT
TGT  TAT  CGT  GGG  AAT  GGC  AAA  AAT  TAT  ATG
GGC  AAC  TTA  TCC  CAA  ACA  AGA  TCT  GGA  CTA
ACA  TGT  TCA  ATG  TGG  GAC  AAG  AAC  ATG  GAA
GAC  TTA  CAT  CGT  CAT  ATC  TTC  TGG  GAA  CCA
GAT  GCA  AGT  AAG  CTG  AAT  GAG  AAT  TAC  TGC
CGA  AAT  CCA  GAT  GAT  GAT  GCT  CAT  GGA  CCC
TGG  TGC  TAC  ACG  GGA  AAT  CCA  CTC  ATT  CCT
TGG  GAT  TAT  TGC  CCT  ATT  TCT  CGT  TGT  GAA
GGT  GAT  ACC  ACA  CCT  ACA  ATA  GTC  AAT  TTA
GAC  CAT  CCC  GTA  ATA  TCT  TGT  GCC  AAA  ACG
AAA  CAA  TTG  CGA  GTT  GTA  AAT  GGG  ATT  CCA
ACA  CGA  ACA  AAC  ATA  GGA  TGG  ATG  GTT  AGT
TTG  AGA  TAC  AGA  AAT  AAA  CAT  ATC  TGC  GGA
GGA  TCA  TTG  ATA  AAG  GAG  AGT  TGG  GTT  CTT
ACT  GCA  CGA  CAG  TGT  TTC  CCT  TCT  CGA  GAC
TTG  AAA  GAT  TAT  GAA  GCT  TGG  CTT  GGA  ATT
CAT  GAT  GTC  CAC  GGA  AGA  GGA  GAT  GAG  AAA
TGC  AAA  CAG  GTT  CTC  AAT  GTT  TCC  CAG  CTG
GTA  TAT  GGC  CCT  GAA  GGA  TCA  GAT  CTG  GTT
TTA  ATG  AAG  CTT  GCC  AGG  CCT  GCT  GTC  CTG
GAT  GAT  TTT  GTT  AGT  ACG  ATT  GAT  TTA  CCT
AAT  TAT  GGA  TGC  ACA  ATT  CCT  GAA  AAG  ACC
AGT  AGC  AGT  GTT  TAT  GGC  TGG  GGC  TAC  ACT
GGA  TTG  ATC  AAC  TAT  GAT  GGC  CTA  TTA  CGA
GTG  GCA  CAT  CTC  TAT  ATA  ATG  GGA  AAT  GAG
AAA  TGC  AGC  CAG  CAT  CAT  CGA  GGG  AAG  GTG
ACT  CTG  AAT  GAG  TCT  GAA  ATA  TGT  GCT  GGG
GCT  GAA  AAG  ATT  GGA  TCA  GGA  CCA  TGT  GAG
GGG  GAT  TAT  GGT  GGC  CCA  CTT  GTT  TGT  GAG
CAA  CAT  AAA  ATG  AGA  ATG  GTT  CTT  GGT  GTC
ATT  GTT  CCT  GGT  CGT  GGA  TGT  GCC  ATT  CCA
AAT  CGT  CCT  GGT  ATT  TTT  GTC  CGA  GTA  GCA
TAT  TAT  GCA  AAA  TGG  ATA  CAC  AAA  ATT  ATT
TTA  ACA  TAT  AAG  GTA  CCA  CAG  TCA  TAG
```

7. An expression vector which comprises the gene coding for human hepatic parenchymal cell growth factor and represented by the base sequence defined in claim 4.

8. A process for producing human hepatic parenchymal cell growth factor, comprising transforming a host cell with the expression vector defined in claim 7, culturing the resulting transformant under conditions suitable for the expression of the growth factor, and recovering the growth factor.

9. The process according to claim 8, wherein the transformation procedures are repeated.

10. The process according to claim 8 or 9, wherein the host cell is an animal cell.

11. An expression vector which comprises a gene coding for human hepatic parenchymal cell growth factor represented by the following amino acid sequence:

Met Trp Val Thr Lys Leu Leu Pro Ala Leu
Leu Leu Gln His Val Leu Leu His Leu Leu
Leu Leu Pro Ile Ala Ile Pro Tyr Ala Glu
Gly Gln Arg Lys Arg Arg Asn Thr Ile His
Glu Phe Lys Lys Ser Ala Lys Thr Thr Leu
Ile Lys Ile Asp Pro Ala Leu Lys Ile Lys
Thr Lys Lys Val Asn Thr Ala Asp Gln Cys
Ala Asn Arg Cys Thr Arg Asn Lys Gly Leu
Pro Phe Thr Cys Lys Ala Phe Val Phe Asp
Lys Ala Arg Lys Gln Cys Leu Trp Phe Pro
Phe Asn Ser Met Ser Ser Gly Val Lys Lys
Glu Phe Gly His Glu Phe Asp Leu Tyr Glu
Asn Lys Asp Tyr Ile Arg Asn Cys Ile Ile
Gly Lys Gly Arg Ser Tyr Lys Gly Thr Val
Ser Ile Thr Lys Ser Gly Ile Lys Cys Gln
Pro Trp Ser Ser Met Ile Pro His Glu His
Ser Phe Leu Pro Ser Ser Tyr Arg Gly Lys
Asp Leu Gln Glu Asn Tyr Cys Arg Asn Pro
Arg Gly Glu Glu Gly Gly Pro Trp Cys Phe
Thr Ser Asn Pro Glu Val Arg Tyr Glu Val
Cys Asp Ile Pro Gln Cys Ser Glu Val Glu
Cys Met Thr Cys Asn Gly Glu Ser Tyr Arg

-continued

| | | | | | | | | | |
|---|---|---|---|---|---|---|---|---|---|
| Gly | Leu | Met | Asp | His | Thr | Glu | Ser | Gly | Lys |
| Ile | Cys | Gln | Arg | Trp | Asp | His | Gln | Thr | Pro |
| His | Arg | His | Lys | Phe | Leu | Pro | Glu | Arg | Tyr |
| Pro | Asp | Lys | Gly | Phe | Asp | Asp | Asn | Tyr | Cys |
| Arg | Asn | Pro | Asp | Gly | Gln | Pro | Arg | Pro | Trp |
| Cys | Tyr | Thr | Leu | Asp | Pro | His | Thr | Arg | Trp |
| Glu | Tyr | Cys | Ala | Ile | Lys | Thr | Cys | Ala | Asp |
| Asn | Thr | Met | Asn | Asp | Thr | Asp | Val | Pro | Leu |
| Glu | Thr | Thr | Glu | Cys | Ile | Gln | Gly | Gln | Gly |
| Glu | Gly | Tyr | Arg | Gly | Thr | Val | Asn | Thr | Ile |
| Trp | Asn | Gly | Ile | Pro | Cys | Gln | Arg | Trp | Asp |
| Ser | Gln | Tyr | Pro | His | Glu | His | Asp | Met | Thr |
| Pro | Glu | Asn | Phe | Lys | Cys | Lys | Asp | Leu | Arg |
| Glu | Asn | Tyr | Cys | Arg | Asn | Pro | Asp | Gly | Ser |
| Glu | Ser | Pro | Trp | Cys | Phe | Thr | Thr | Asp | Pro |
| Asn | Ile | Arg | Val | Gly | Tyr | Cys | Ser | Gln | Ile |
| Pro | Asn | Cys | Asp | Met | Ser | His | Gly | Gln | Asp |
| Cys | Tyr | Arg | Gly | Asn | Gly | Lys | Asn | Tyr | Met |
| Gly | Asn | Leu | Ser | Gln | Thr | Arg | Ser | Gly | Leu |
| Thr | Cys | Ser | Met | Trp | Asp | Lys | Asn | Met | Glu |
| Asp | Leu | His | Arg | His | Ile | Phe | Trp | Glu | Pro |
| Asp | Ala | Ser | Lys | Leu | Asn | Glu | Asn | Tyr | Cys |
| Arg | Asn | Pro | Asp | Asp | Asp | Ala | His | Gly | Pro |
| Trp | Cys | Tyr | Thr | Gly | Asn | Pro | Leu | Ile | Pro |
| Trp | Asp | Tyr | Cys | Pro | Ile | Ser | Arg | Cys | Glu |
| Gly | Asp | Thr | Thr | Pro | Thr | Ile | Val | Asn | Leu |
| Asp | His | Pro | Val | Ile | Ser | Cys | Ala | Lys | Thr |
| Lys | Gln | Leu | Arg | Val | Val | Asn | Gly | Ile | Pro |
| Thr | Arg | Thr | Asn | Ile | Gly | Trp | Met | Val | Ser |
| Leu | Arg | Tyr | Arg | Asn | Lys | His | Ile | Cys | Gly |
| Gly | Ser | Leu | Ile | Lys | Glu | Ser | Trp | Val | Leu |
| Thr | Ala | Arg | Gln | Cys | Phe | Pro | Ser | Arg | Asp |
| Leu | Lys | Asp | Tyr | Glu | Ala | Trp | Leu | Gly | Ile |
| His | Asp | Val | His | Gly | Arg | Gly | Asp | Glu | Lys |
| Cys | Lys | Gln | Val | Leu | Asn | Val | Ser | Gln | Leu |
| Val | Tyr | Gly | Pro | Glu | Gly | Ser | Asp | Leu | Val |
| Leu | Met | Lys | Leu | Ala | Arg | Pro | Ala | Val | Leu |
| Asp | Asp | Phe | Val | Ser | Thr | Ile | Asp | Leu | Pro |
| Asn | Tyr | Gly | Cys | Thr | Ile | Pro | Glu | Lys | Thr |
| Ser | Cys | Ser | Val | Tyr | Gly | Trp | Gly | Tyr | Thr |

-continued

| | | | | | | | | | |
|---|---|---|---|---|---|---|---|---|---|
| Gly | Leu | Ile | Asn | Tyr | Asp | Gly | Leu | Leu | Arg |
| Val | Ala | His | Leu | Tyr | Ile | Met | Gly | Asn | Glu |
| Lys | Cys | Ser | Gln | His | His | Arg | Gly | Lys | Val |
| Thr | Leu | Asn | Glu | Ser | Glu | Ile | Cys | Ala. | Gly |
| Ala | Glu | Lys | Ile | Gly | Ser | Gly | Pro | Cys | Glu |
| Gly | Asp | Tyr | Gly | Gly | Pro | Leu | Val | Cys | Glu |
| Gln | His | Lys | Met | Arg | Met | Val | Leu | Gly | Val |
| Ile | Val | Pro | Gly | Arg | Gly | Cys | Ala | Ile | Pro |
| Asn | Arg | Pro | Gly | Ile | Phe | Val | Arg | Val | Ala |
| Tyr | Tyr | Ala | Lys | Trp | Ile | His | Lys | Ile | Ile |
| Leu | Thr | Tyr | Lys | Val | Pro | Gln | Ser | * | |

12. A process for producing human hepatic parenchymal cell growth factor, comprising transforming a host cell with the expression vector defined in claim 11, culturing the resulting transformant under conditions suitable for the expression of the growth factor, and recovering the growth factor.

13. The process according to claim 12, wherein the transformation procedures are repeated.

14. The process according to claim 12 or 13, wherein the host cell is an animal cell.

15. Expression plasmid pKCRHGF-2.

16. An animal cell which is transformed with the expression vector according to claim 11 or 7 or the plasmid according to claim 15 and produces human hepatic parenchymal cell growth factor.

17. An animal cell which is obtained by repeated transformation with the expression vector according to claim 11 or 7 or the plasmid according to claim 15 and which produces human hepatic parenchymal cell growth factor.

* * * * *